| (12) | United States Patent | (10) Patent No.: | US 12,370,254 B2 |
|---|---|---|---|
| | Yao | (45) Date of Patent: | Jul. 29, 2025 |

(54) DENDRITIC CELL-TARGETING UNIVERSAL VACCINE FOR INFLUENZA INFECTION

(71) Applicant: University of Manitoba, Winnipeg (CA)

(72) Inventor: Xiao-Jian Yao, Winnipeg (CA)

(73) Assignee: University of Manitoba, Winnipeg (CA)

( * ) Notice: Subject to any disclaimer, the term of this patent is extended or adjusted under 35 U.S.C. 154(b) by 314 days.

(21) Appl. No.: 17/768,624

(22) PCT Filed: Oct. 21, 2020

(86) PCT No.: PCT/CA2020/051409
§ 371 (c)(1),
(2) Date: Apr. 13, 2022

(87) PCT Pub. No.: WO2021/077215
PCT Pub. Date: Apr. 29, 2021

(65) Prior Publication Data
US 2024/0181045 A1 Jun. 6, 2024

Related U.S. Application Data

(60) Provisional application No. 62/923,842, filed on Oct. 21, 2019.

(51) Int. Cl.
| C07K 14/005 | (2006.01) |
| A61K 39/00 | (2006.01) |
| A61K 39/145 | (2006.01) |
| A61K 39/295 | (2006.01) |
| A61P 37/04 | (2006.01) |
| C07K 14/11 | (2006.01) |

(52) U.S. Cl.
CPC .......... *A61K 39/295* (2013.01); *A61K 39/145* (2013.01); *A61P 37/04* (2018.01); *C07K 14/005* (2013.01); *A61K 2039/5258* (2013.01); *C07K 2319/00* (2013.01); *C12N 2760/14122* (2013.01); *C12N 2760/14134* (2013.01); *C12N 2760/16122* (2013.01); *C12N 2760/16134* (2013.01)

(58) Field of Classification Search
CPC ............ A61K 2039/5258; A61K 39/12; A61K 2039/6075; A61K 39/145; A61K 39/295
See application file for complete search history.

(56) References Cited

FOREIGN PATENT DOCUMENTS

WO 2019/113688 6/2019

OTHER PUBLICATIONS

Carter, DM et al. Design and Characterization of a Computationally Optimized Broadly Reactive Hemagglutinin Vaccine for H1N1 Influenza Viruses. Journal of Virology. Epub. Feb. 24, 2016, vol. 90, No. 9, pp. 4720-4734.
Wong, TM et al. Computationally optimized broadly reactive hemagglutinin elicits hemagglutination inhibition antibodies against a panel of H3N2 influenza virus cocirculating variant. Journal of Virology Epub Oct. 4, 2017, vol. 91, No. 24, pp. 1-18.
Giles, BM et al. Antibody Breadth and Protective Efficacy are Increased by Vaccination with Computationally Optimized Hemagglutinin but Not with Polyvalent Hemagglutinin-Based H5N1 Virus-Like Particle Vaccines. Clinical and Vaccine Immunology Epub. Dec. 21, 2011, vol. 19, No. 2, pp. 128-139.
Martinez, O et al. Impact of Ebla Mucin-Like Domain on Antiglycoprotein Antibody Responses Induced by Ebola Virus-Like Particles, Nov. 1, 2011, vol. 204, No. 3, pp. S825-S832.
Sautto, GA et al. Towards a universal influenza vaccine: different approaches for one goal Jan. 19, 2018, vol. 15, No. 1, pp. 1-12.
Zhang, Y el al. Targeting Hemagglutinin: Approaches for Board Protection against the Influenza A Virus Apr. 30, 2019, vol. 11, No. 405, pp. 1-24.

*Primary Examiner* — Barry A Chestnut
(74) *Attorney, Agent, or Firm* — Michael R Williams; Ryan W Duplin; Ade & Company Inc.

(57) ABSTRACT

We have recently developed a novel DC-targeting vaccine platform using Ebola glycoprotein (EboGP) DC-targeting domain-based fusion protein technology. Here, we will use this technology to generate universal vaccines against Influenza A by fusing a DC-targeting/activation domain (EboG-PAM), derived from EboGP to I) a tetrameric conserved extracellular domain of M2 (M2e) of Influenza A strains from human, birds, and swine; 2) the conserved stalk regions (HAcs) of HA and an M2 polypeptide from H5N1 strain; and 3) the HA head regions polypeptides ($HA_{H5-1-3}$) derived from H5N1, H1 N1 and H3N2 strains.

17 Claims, 9 Drawing Sheets

Specification includes a Sequence Listing.

Influenza HA

Head regions

Stalk regions

B.

| Virus | subtype | M2e |
|---|---|---|
| Human virus M2e consensus | N/A | MSLLTEVETPIRNEWGCRCND |
| A/Phillipines/2/82 | H3N2 | MSLLTEVETPIRNEWGCRCND |
| A/Puerto Rico/8/34 | H1N1 | MSLLTEVETPIRNEWGCRCNG |
| A/California/04/09 | H1N1 | MSLLTEVETPTRNEWECRCSD |
| A/Vietnam/1203/04 | H5N1 | MSLLTEVETPTRNEWECRCSD |

C. Selected Flu Head COBRA H5/H1/H3 regions

-GPGPG-

H5EKTHNGKLCDLDGVKPLILRDCSVAGWLLGNPMCDEFINVPEWSYIVEKANPANDLCYPGN-

GPGPG_H1CYPGYFADYEELREQLSSVSSFERFEIFPKESSWPNHTVT_GPGPG_H1EKEVLVLWGVHHPSNI-

GPGPG_H1PKVRDQEGRINYYWTLLEPGDTIIFEANGNLIAPWYAFALS_GPGPG_H3NNEKFDKLYIWGVHH

PGTDSDQISLYAQASGRITVSTKRSQQTVIPNIGSRPRVRDVSSRISIYWTIVKPGDILLINSTGNLIAPRG

YFKIRS_GPGPG_

Selected HA Stalk region/M2eh regions

GPGPSA_EQVDTIMEKNVTVTHAQDILEKTH-GSA_INSSMPFHNIHPLTIGECPKYVKSNRLVLATGLRN

SP_GSA_SLLTEVETPIRNEWGCRCN-GSA_STQKAIDGVTNKVNSIIDKMNTQFEAVGREFNNLER

RIENLNKKMEDGFLDVWTYNAELLVLMENERTLDFHDSNVKNLYDKVRRQLRDNAKELGN-GSA

Selected Flu M2e-(Human/birds/Swine) regions

GGSLLTEVETPIRNEWGCRCNDSSD-GGGS-SLLTEVETPTRNGWECKCSDSSD-GGGS-

SLLTEVETPIRNEWGCRCNDSSD-GGGS-SLLTEVETPIRNGWECRCNDSSD-GGGS

DENDRITIC CELL-TARGETING UNIVERSAL VACCINE FOR INFLUENZA INFECTION

PRIOR APPLICATION INFORMATION

The instant application is a 371 of PCT Application CA2020/051409, filed Oct. 21, 2020, which claimed the benefit of US Provisional Patent Application U.S. Ser. No. 62/923,842, filed Oct. 21, 2019, and entitled "Dendritic Cell-Targeting Universal Vaccine for Influenza Infection", the entire contents of which are incorporated herein by reference for all purposes.

BACKGROUND OF THE INVENTION

Influenza virus disease is caused by the influenza virus which has four types including Influenza A, B, C and D among which influenza A and B are of economic and medical importance to humans (7). Surprisingly, 100 years after a major pandemic infection caused by influenza virus A killed approximately 50 million people globally in 1918 (18, 28), influenza virus infection still poses a high threat to the health sector globally (39). According to the Centre for Disease Control (CDC), there are still pediatric deaths and young people deaths associated with influenza H1N1 and H3N2 strains (6). Although the fatality rate from influenza virus is low compared to previous years in the US, developing countries and underdeveloped countries still have high levels of influenza infection, and there is still fear of emergence of a new strain of influenza virus as long as different influenza virus strains are still in circulation. It is noteworthy that the reduction in the number of cases of influenza virus infection experienced currently is due to the availability of the annual vaccine; however, there are some issues regarding administration of this vaccine. For example, some of these limitations include vaccine mismatch, production of vaccine based on predictions which may not be always be accurate and the financial implications on the government and the psychological effect on the populace who have to receive flu shot every year for their entire life. Moreover, this effort has not successfully eradicated the influenza virus infection and may not be able to eliminate it (16, 44). Based on this, CDC, as part of their recent recommendations, emphasizes the need for a universal vaccine against influenza viral infection (16).

The universal vaccine is characterized by the ability to protect individuals from different strains and subtypes of influenza virus. In addition to the different types of influenza virus, each type has a family of different strains, of which influenza A has the most abundant family (12). The variation in the various strains of influenza occurs at the hemagglutinin (HA) and neuraminidase (NA) domains. Influenza A has eighteen (18) known HA antigens, and eleven (11) identified NA antigens with different host ranges including human, birds, bats, and swine (35). The difficulty in the production of a universal vaccine against influenza virus has been due to the mutation and reassortment peculiarity of influenza virus which changes the conformation of the antigen in phenomena known as antigenic shift (caused by reassortment) and antigenic drift (caused by mutation) and consequently allows influenza virus to continuously escape the host immune defence system (33). Therefore, to develop a universal vaccine, conserved components on the surface protein of influenza must be used to elicit immune responses that can bind with the same antigens on all of the strains of influenza virus. In the development of influenza vaccines, much attention is placed on the HA domain because of its tendency to also induce neutralization antibodies (26). Influenza virus HA has two regions: the unstable globular head region (amino acids 59-229) and the conserved stalk region (amino acids 18-58 and 530-566). The globular head region is unstable due to mutation and reassortment peculiarity of influenza A and is the principal factor for the setbacks in the development of universal vaccine; however, the stalk region of HA is highly conserved among strains of influenza virus and focus has been placed on this for the development of universal vaccines against influenza virus (10, 38). Moreover, among the surface proteins of influenza virus is a conserved extracellular domain, Matrix-2 (M2), which has also been found promising in the development of a universal vaccine for influenza viral infection due to its stability (10, 38).

Although many studies have used this information as basis to develop universal influenza vaccine using different approaches including, an influenza M2 (36) and HA fusion protein; targeting conserved broadly reactive epitopes on the HA stalk (19); influenza M2e and bacterial flagellin fusion protein (37); recombinant HA expressed as a virus-like particle (VLP) (45); and computationally optimized broadly reactive antigen (COBRA) HA vaccine (9) among others, these methods have had varying limitations, with the majority having low immune response boost except if used with adjuvants such as MF59 and ASO3 (33). However, adjuvanted vaccines can have side effects on patients. For example, as mentioned by Nohynek et al. in her study among children administered with H1N1 vaccine adjuvanted with ASO3, they found narcolepsy associated among the child subjects (29). Therefore, the search for stronger immunogens with broad protection against all strains of influenza virus with little or no side effects is still very paramount.

To address this problem, there is a recent diversion of attention to the induction of stronger immune response by targeting the influenza antigen towards dendritic cells (DCs). The DC-targeting vaccine has of recent received global attention, and several works are in the pipeline for the development and production of vaccine by targeting the desired antigen to the DCs including adenovirus (8), cancer (5), Dengue virus (48), and yellow fever (31), among others. This approach is effective because of the ability of DCs to act as antigen-presenting cells (APCs) to stimulate the adaptive immune responses, including humoral immune responses, and the regulation of innate immune responses. Thus, there is a need for a novel approach that can both confer broad and robust protection against current and future strains of influenza virus.

SUMMARY OF THE INVENTION

According to a first aspect of the invention, there is provided a fusion protein comprising an influenza virus surface protein peptide inserted in the mucin-like domain of a Filoviridae Virus glycoprotein wherein the influenza virus surface protein is selected from the group consisting of hemagglutinin and matrix-2 and the influenza virus surface protein peptide comprises 6 or more consecutive amino acids of the surface protein sequence.

In some embodiments, the influenza virus surface peptide comprises 6 or more consecutive amino acids of a conserved region (stalk region) of hemagglutinin or matrix-2 or 6 or more consecutive amino acids of globular head domain of hemagglutinin.

In some embodiments of the invention, the fusion peptide comprises more than one influenza virus surface protein peptide and each respective influenza virus surface protein peptide is separated from an adjacent influenza virus surface protein peptide by a spacer.

In some embodiments, the influenza virus surface protein peptide is separated from the Filoviridae Virus glycoprotein peptide(s) by a spacer.

In some embodiments, the mucin-like domain comprises amino acids 305-501 of the Ebola Virus glycoprotein.

In some embodiments, the mucin-like domain consists of amino acids 305-501 of the Ebola virus glycoprotein.

In some embodiments, the mucin-like domain comprises amino acids 257-501 of Marburg virus glycoprotein.

In some embodiments, the mucin-like domain consists of amino acids 257-501 of Marburg virus glycoprotein.

In some embodiments, the mucin-like domain is a tolerated deletion of the mucin-like domain. That is, in some embodiments, the protein of interest, that is, a fusion peptide as described herein, is not only inserted in frame into the mucin-like domain of the Filoviridae glycoprotein, the peptide or protein of interest also replaces at least some of the mucin-like domain. That is, as discussed below, the peptide or protein of interest is inserted in frame into a tolerated deletion of the mucin-like domain, as discussed herein.

In some embodiments, there is provided a nucleic acid encoding the fusion protein described above.

In some embodiments, there are provided virus-like particles comprising the fusion protein described above.

According to another aspect of the invention, there is provided a method of targeting an influenza virus surface protein peptide to a dendritic cell comprising: providing virus-like particles comprising as glycoprotein a Filoviridae Virus glycoprotein fusion protein comprising an influenza virus surface protein peptide inserted in the mucin-like domain of the Filoviridae Virus glycoprotein wherein the influenza virus surface protein is selected from the group consisting of hemagglutinin and matrix-2 and the influenza virus surface protein peptide comprises 6 or more consecutive amino acids of the influenza virus surface protein sequence; and immunizing an individual in need of immunization against the influenza virus with an effective amount of the virus-like particles.

In some embodiments, the fusion peptide comprises more than one influenza virus surface protein peptide and each respective influenza virus surface protein peptide is separated from an adjacent influenza virus surface protein peptide by a spacer.

According to another aspect of the invention, there is provided use of virus-like particles comprising as glycoprotein a Filoviridae Virus glycoprotein fusion protein comprising an influenza virus surface protein peptide inserted in the mucin-like domain of the Filoviridae Virus glycoprotein wherein the influenza virus surface protein is selected from the group consisting of hemagglutinin and matrix-2 and the influenza virus surface protein peptide comprises 6 or more consecutive amino acids of the influenza virus surface protein sequence; for targeting the influenza virus surface protein peptide to a dendritic cell.

In some embodiments of the invention, the fusion peptide comprises more than one influenza virus surface protein sequence and each respective influenza virus surface protein sequence is separated from an adjacent influenza virus surface protein sequence by a spacer.

According to another aspect of the invention, there is provided a method of eliciting an enhanced immune response against an influenza surface protein peptide comprising:

providing virus-like particles comprising as glycoprotein a Filoviridae Virus glycoprotein fusion protein comprising an influenza virus surface protein peptide inserted in the mucin-like domain of the Filoviridae Virus glycoprotein wherein the influenza virus surface protein is selected from the group consisting of hemagglutinin and matrix-2 and the influenza virus surface protein peptide comprises 6 or more consecutive amino acids of the influenza virus surface protein sequence; and immunizing an individual in need of immunization against influenza virus with an effective amount of the virus-like particles.

In some embodiments, the fusion peptide comprises more than one influenza virus surface protein peptide and each respective influenza virus surface protein peptide is separated from an adjacent influenza virus surface protein peptide by a spacer.

According to another aspect of the invention, there is provided use of a Filoviridae Virus glycoprotein fusion protein comprising an influenza virus surface protein peptide inserted in the mucin-like domain of the Filoviridae Virus glycoprotein wherein the influenza virus surface protein is selected from the group consisting of hemagglutinin and matrix-2 and the influenza virus surface peptide comprises 6 or more consecutive amino acids of the influenza virus surface protein sequence; for eliciting an enhanced or increased immune response against the influenza virus surface protein.

As will be appreciated by one of skill in the art, the increased or enhanced immune response may be in an individual, in particular, an individual in need of immunization against influenza virus, wherein the individual may be a human.

As will be appreciated by one of skill in the art, an individual in need of such treatment may be an individual who is at risk of being exposed to the influenza virus or who is in a high risk group as defined by the WHO and/or an individual who gets the annual flu shot, for example, pregnant women, children 5 years of age and younger, the elderly, health care workers and people who have chronic illnesses or are immunocompromised.

In some embodiments, the Filoviridae virus is Ebola virus or Marburg virus.

According to another aspect of the invention, there is provided a method of targeting a peptide of interest to an antigen presenting cell comprising:

preparing a fusion protein comprising a Filoviridae Virus glycoprotein comprising an influenza surface protein peptide inserted in the mucin-like domain of the Filoviridae Virus glycoprotein wherein the influenza virus surface protein is selected from the group consisting of hemagglutinin and matrix-2 and the influenza virus surface peptide comprises 6 or more consecutive amino acids of the influenza virus surface protein sequence;

assembling virus-like particles comprising the fusion protein; and immunizing an individual in need of immunization against the peptide of interest with an effective amount of the virus-like particles.

In some embodiments, the fusion peptide comprises more than one influenza virus surface protein peptide and each respective influenza virus surface protein peptide is separated from an adjacent influenza virus surface protein peptide by a spacer.

According to another aspect of the invention, there is provided use of a fusion protein comprising a Filoviridae Virus glycoprotein comprising an influenza virus surface protein peptide inserted in the mucin-like domain of the Filoviridae Virus glycoprotein wherein the influenza virus surface protein is selected from the group consisting of hemagglutinin and matrix-2 and the influenza virus surface protein peptide comprises 6 or more consecutive amino acids of the influenza virus surface protein sequence; for targeting the influenza virus surface protein peptide to a dendritic cell.

In some embodiments, the fusion peptide comprises more than one influenza virus surface protein peptide and each respective influenza virus surface protein peptide is separated from an adjacent influenza protein peptide by a spacer.

According to another aspect of the invention, there is provided a method of eliciting an immune response against an influenza virus surface protein comprising:

preparing a fusion protein comprising a Filoviridae Virus glycoprotein comprising an influenza surface protein peptide inserted in the mucin-like domain of the Filoviridae Virus glycoprotein wherein the influenza virus surface protein is selected from the group consisting of hemagglutinin and matrix-2 and the influenza virus surface protein peptide comprises 6 or more consecutive amino acids of the influenza virus surface protein sequence;

assembling virus-like particles comprising the fusion protein; and immunizing an individual in need of immunization against influenza virus with an effective amount of the virus-like particles.

In some embodiments, the fusion peptide comprises more than one influenza virus surface protein peptide and each respective influenza virus surface protein peptide is separated from an adjacent influenza virus surface protein peptide by a spacer.

BRIEF DESCRIPTION OF THE DRAWINGS

FIG. 1: Schematic diagram and representation of various conserved epitopes in influenza HA and M2 proteins: A) Schematic structure of a monomeric hemagglutinin (HA) of influenza A, consisting of Head region and the stalk region. (B) Influenza A M2e amino acids from different strains (43) (C) polypeptides comprising amino acid sequences of the selected Flu head regions from COBRA H5 and H1 sequences/H3 sequences (total 251 aa). The middle panel: The amino acids of the polypeptides comprises the influenza HA Stalk region of subtype H5 (176 aa). The lower panel is the amino acids of tetrameric M2e regions polypeptide selected from M2e of Matrix 2 protein (Human/birds/human/swine (in this order) (92 aa)). Between each selected peptide was linked by a glycine-proline-glycine-proline-glycine (GPGPG) spacer.

FIG. 5: Antibodies induced in immunized mice by EboGPΔM-HAcsM2e partially inhibit influenza H1N1 virus: The pooled sera (in two folds serially dilutions) of the immunized mice were incubated with H1N1 virus (25 PFU/ml (A), and 50 PFU/ml (B) for 1 hour in 37° C. and 5% CO$_2$ and then the sera/viral mixtures were used to infect the MDCK cells at about 90% confluent for 1 hour. Then, the infected cells were covered by AVICEL After 72 hours of incubation, the cells were fixed with 4% formaldehyde for 20 minutes, stained with crystal violet, and observed for plaque formation.

FIG. 6: Cytokines and chemokines were produced by splenocytes in EbovGPΔMuc-M2 and EbovGPΔMuc-HM2-immunized mice after in vitro stimulation with Influenza HA or M2 peptides: Splenocytes were isolated from the immunized mice and were stimulated for 72 hours with influenza HA peptides or M2 peptides while the negative control was not stimulated. After stimulation, cytokines and cytokines released were detected in the supernatants using a multiplex cytokine detection kit and counted in the MAGPIX instrument.

FIG. 9: VLP-EboGPΔM-H5-1-3 and VSV-EboGPΔM-HAcsM2e vaccines induced more robust anti-HA antibody responses than the native HA/NA/M2 VLPs. The Balb/c mice were injected subcutaneously with 100 ng of EboGPΔM-H5-1-3 VLP or Native HA/NA/M2 or PBS, or intramuscularly $1\times10^7$ tissue culture infectious dose of 50% (TCID$_{50}$) of EboGPΔM-HAcsM2e VSV. Balb/c mice were immunized on Day 0 and boosted on Day 28. Blood was collected on day 35 after the immunization to investigate the anti-HA antibody-induced using ELISA. A 96 well-plate was coated with 0.5 µg of HA recombinant protein from H5N1 overnight at 4° C. (A) The HA antibody in the sera was detected using the ELISA technique, using IgG secondary antibody. (B) The HA antibody in the nasal wash was detected using the ELISA technique, using anti-IgA secondary antibody. (C) Sera collected from each group of mice that received the immunization were pooled together and, anti-HA IgG antibodies against H1, H3 and H5 strains of influenza virus were detected using ELISA coating with 0.5 µg of HA recombinant proteins from H1N1 (left panel), H3N2 (middle panel) or H5N1 (right panel). Statistical significance was determined using an unpaired t-test, and significant p values were shown as P≥0.001 or P≥0.01.

DESCRIPTION OF THE PREFERRED EMBODIMENTS

Figure 2:
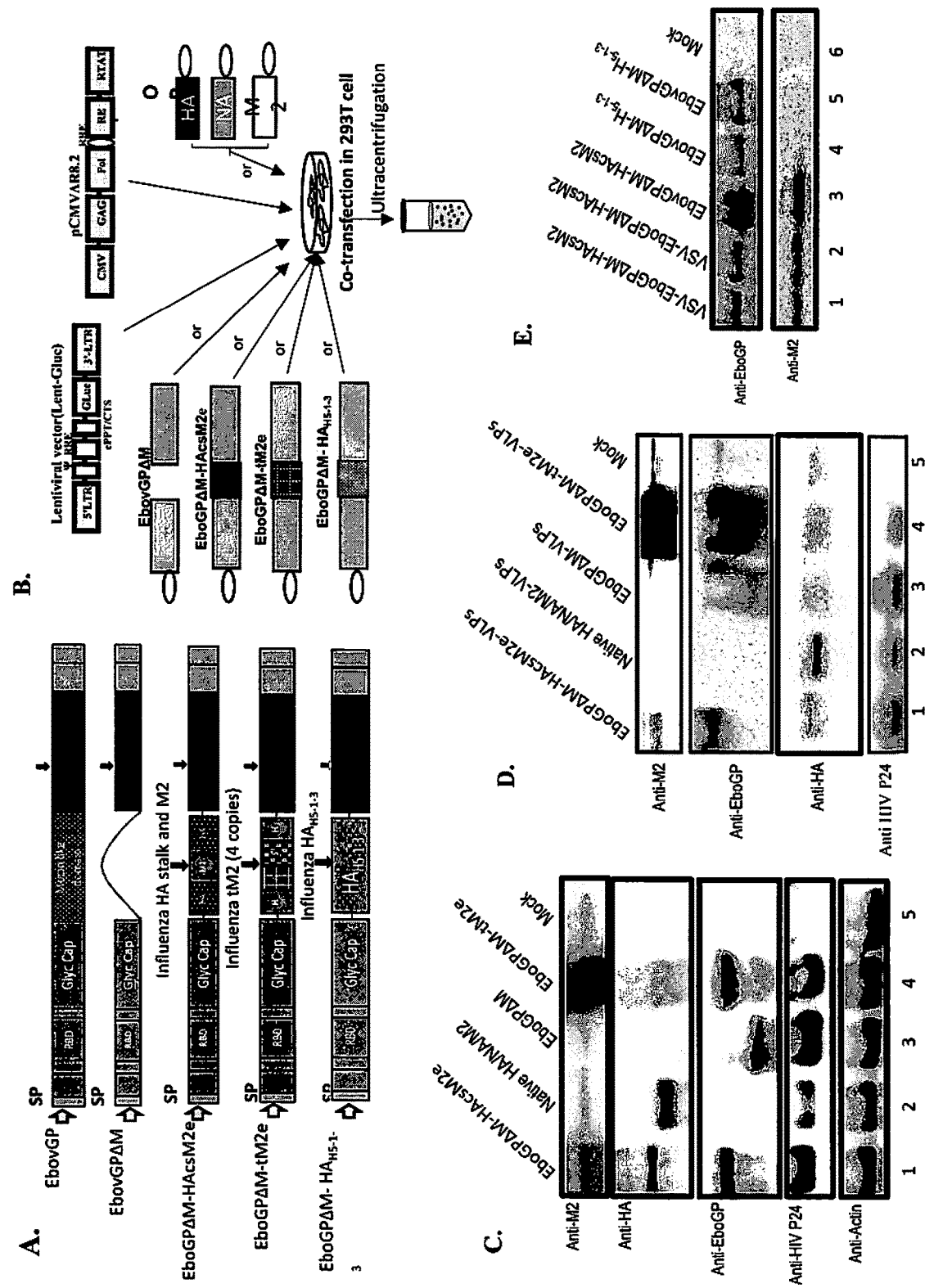
FIG. 2: The schematic construction of EboGPΔM-HA$_{H5-1-3}$, EboGPΔM-HAcsM2e and EBOVGPΔM-tM2e expressing plasmids and production of each pseudotyped VLPs A) The Schematic structures and construction of various plasmids encoding EboGPΔM-HAcsM2e and EboGPΔM-tM2e and EboGPΔM-HA$_{H5-1-3}$ chimeric protein. B). Schematic procedure of production of EboGPΔM-HAcsM2e- or EboGPΔM-tM2e-, orEboGPΔM-HA$_{H5-1}$-pseudotyped VLPs. 293T cells were co-transfected by HIV-1ΔRI/ΔE/Gluc+provirus, CMV-Gag-Pol and each of EboGPΔM-HAcsM2e, EboGPΔM-tM2e or EboGPΔM-HA$_{H5-1-3}$ expressing plasmids. At 48 hrs post-transfection, supernatant containing VLPs were collected, and used to infect various cells, including dendritic cells and macrophages, or for immunization experiments of mice. Gluc: *Gaussia* luciferase. C-E) Detection of the expression of EboGPΔM-HAcsM2e, EboGPΔM-tM2e and EboGPΔM-HA$_{H5-1-3}$ fusion proteins. Each co-transfected 293T cells and collected VLPs were lysed and analyzed by WB with anti-HA, and anti-M2, anti-EboGP or anti-HIVp24 antibody separately.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Given the fact that targeting dendritic cells (DCs) have shown high potential to stimulate stronger immune responses, our laboratory has developed a novel DCs/macrophage-targeting vaccine platform based on EboGP DC-targeting domain-based fusion protein technology. Some particular receptors have been identified for EboGP, including dendritic cell-specific ICAM-3-grabbing non-integrin (DC-SIGN), acetylgalactosamine-specific C-type lectin (hMGL), and asialoglycoprotein receptor 1 (ASGPRI) and human macrophage galactose (30, 32).

Specifically, Published PCT Application WO 2019/113688, incorporated herein by reference for its teachings regarding the EboGP expression system, describes a series of Marburgvirus envelope glycoprotein (MarvGP)-based and Ebolavirus envelope glycoprotein (EboGP)-based chimeric fusion proteins that are still able to maintain an efficient EboGP-mediated virus entry in various cell types including human antigen-presenting cells (APCs) and macrophages, while presenting large polypeptides at the apex and the sides of each EboGP monomer.

As discussed therein, the mucin-like domain is generally accepted as encompassing residues 305 or 308 to 501 of the EboGP peptide sequence and amino acid residues 257-501 of the Marburg virus. (13). For example, the deletion of 178 amino acids within the mucin-like domain permits the insertion of larger peptides. That is, deletion of these 178 amino acids and replacement thereof with an antigenic peptide of interest results in the peptide of interest being presented or displayed or expressed at the apex and sides of the glycoprotein monomer. This is an example of what is referred to therein and herein as "tolerated deletions", that is, deletions of amino acids within the mucin-like domain that do not significantly impair presentation or display of the inserted peptide at the apex and sides of the fusion glycoprotein. Other suitable tolerated deletions will be apparent to one of skill in the art and/or can be confirmed or determined using routine experimentation.

EboGP can be efficiently incorporated into retroviral particles resulting in significantly facilitated cell entry in human DCs and macrophages, and stimulating significantly higher immune responses (4). Previously, it was known that the MLD domain or a tolerated deletion thereof could be replaced by heterologous peptide in order to target peptides to antigen-presenting cells, but it was not known if inserted peptides could be targeted specifically to dendritic cells. As discussed herein, targeting to dendritic cells is critical for generating an immune response against a peptide that has traditionally generated a poor immune response.

According to an aspect of the invention, there is provided a fusion protein comprising an influenza virus surface protein peptide inserted in the mucin-like domain of a Filoviridae Virus glycoprotein wherein the influenza virus surface protein is selected from the group consisting of hemagglutinin and matrix-2 and the influenza virus surface protein peptide comprises 6 or more consecutive amino acids of the influenza virus surface protein sequence.

In some embodiments, the influenza virus surface protein peptide comprises 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more or 25 or more consecutive amino acids of the surface protein sequence.

In some embodiments, the influenza virus surface protein peptide comprises 6 or more consecutive amino acids of a conserved region of hemagglutinin or matrix-2 or 6 or more consecutive amino acids of globular head domain of hemagglutinin.

In some embodiments, the fusion peptide comprises more than one influenza virus surface protein peptide and each respective influenza virus surface protein peptide is separated from an adjacent influenza virus protein peptide by a spacer.

In some embodiments of the invention, the influenza virus surface protein peptide is separated from the Filoviridae Virus glycoprotein peptide(s) by a spacer.

In some embodiments, the mucin-like domain comprises amino acids 305-501 of the Ebola Virus glycoprotein.

In some embodiments, the mucin-like domain consists of amino acids 305-501 of the Ebola virus glycoprotein.

In some embodiments, the mucin-like domain comprises amino acids 257-501 of Marburg virus glycoprotein.

In some embodiments, the mucin-like domain consists of amino acids 257-501 of Marburg virus glycoprotein.

In some embodiments, the mucin-like domain is a tolerated deletion of the mucin-like domain. That is, in some embodiments, the protein of interest is not only inserted in frame into the mucin-like domain of the Filoviridae glycoprotein, the peptide or protein of interest also replaces at least some of the mucin-like domain. That is, as discussed below, the peptide or protein of interest is inserted in frame into a tolerated deletion of the mucin-like domain, as discussed herein.

In some embodiments of the invention, the tolerated deletion is amino acids 305-483 of the Ebola glycoprotein. However, as discussed herein and as will be apparent to one of skill in the art, other tolerated deletions of the mucin-like domain may be used within the invention.

In some embodiments, there is provided a nucleic acid encoding the fusion protein described above.

In some embodiments, there is provided a virus-like particle comprising the fusion protein described above.

According to another aspect of the invention, there is provided a method of targeting an influenza virus surface protein peptide to a dendritic cell comprising: providing virus-like particles comprising as glycoprotein a Filoviridae Virus glycoprotein fusion protein comprising an influenza virus surface protein peptide inserted in the mucin-like domain of the Filoviridae Virus glycoprotein wherein the influenza virus surface protein is selected from the group consisting of hemagglutinin and matrix-2 and the influenza virus surface protein peptide comprises 6 or more consecutive amino acids of the influenza virus surface protein sequence; and
  immunizing an individual in need of immunization against the influenza virus with an effective amount of the virus-like particles.

According to another aspect of the invention, there is provided use of virus-like particles comprising as glycoprotein a Filoviridae Virus glycoprotein fusion protein comprising an influenza virus surface protein peptide inserted in the mucin-like domain of the Filoviridae Virus glycoprotein wherein the influenza virus surface protein is selected from the group consisting of hemagglutinin and matrix-2 and the influenza virus surface protein peptide comprises 6 or more consecutive amino acids of the influenza virus surface protein sequence; for targeting the influenza virus surface protein peptide to a dendritic cell.

According to another aspect of the invention, there is provided a method of eliciting an immune response against an influenza surface protein peptide comprising: providing a virus-like particle comprising as glycoprotein a Filoviridae Virus glycoprotein fusion protein comprising an influenza virus surface protein peptide inserted in the mucin-like domain of the Filoviridae Virus glycoprotein wherein the influenza virus surface protein is selected from the group consisting of hemagglutinin and matrix-2 and the influenza virus surface protein peptide comprises 6 or more consecutive amino acids of the influenza virus surface protein sequence; and
  immunizing an individual in need of immunization against influenza virus with an effective amount of the virus-like particles.

In some embodiments, the Filoviridae virus is Ebola virus or Marburg virus.

According to another aspect of the invention, there is provided use of a Filoviridae Virus glycoprotein fusion protein comprising an influenza surface protein peptide inserted in the mucin-like domain of the Filoviridae Virus glycoprotein wherein the influenza surface protein is selected from the group consisting of hemagglutinin and matrix-2 and the influenza virus surface protein peptide comprises 6 or more consecutive amino acids of the influenza virus surface protein sequence; for eliciting an immune response against the influenza virus surface protein.

As will be appreciated by one of skill in the art, the immune response may be in an individual, in particular, an individual in need of immunization against influenza virus, wherein the individual may be a human.

As will be appreciated by one of skill in the art, an individual in need of such treatment may be an individual who is at risk of being exposed to the influenza virus or who is in a high risk group as defined by the WHO and/or an individual who gets the annual flu shot, for example, pregnant women, children 5 years of age and younger, the elderly, health care workers and people who have chronic illnesses or are immunocompromised.

Furthermore, as discussed herein, the immune response may be increased or enhanced compared to the immune response obtained from immunizing an individual of similar age and general condition with the influenza virus surface protein peptide without insertion in the mucin-like domain.

In some embodiments, the Filoviridae virus is Ebola virus or Marburg virus.

According to another aspect of the invention, there is provided a method of targeting an influenza virus surface protein peptide to a dendritic cell comprising: preparing a fusion protein comprising a Filoviridae Virus glycoprotein comprising an influenza surface protein peptide inserted in the mucin-like domain of the Filoviridae Virus glycoprotein wherein the influenza virus surface protein is selected from the group consisting of hemagglutinin and matrix-2 and the influenza virus surface protein peptide comprises 6 or more consecutive amino acids of the influenza virus surface protein sequence;
  assembling virus-like particles comprising the fusion protein; and
  immunizing an individual in need of immunization against the peptide of interest with an effective amount of the virus-like particles.

In some embodiments, the Filoviridae virus is Ebola virus or Marburg virus.

According to another aspect of the invention, there is provided use of a fusion protein comprising a Filoviridae Virus glycoprotein comprising an influenza virus surface protein peptide inserted in the mucin-like domain of the Filoviridae Virus glycoprotein wherein the influenza virus surface protein is selected from the group consisting of hemagglutinin and matrix-2 and the influenza virus surface protein peptide comprises 6 or more consecutive amino acids of the influenza virus surface protein sequence; for targeting the influenza virus surface protein peptide to a dendritic cell.

In some embodiments, the fusion peptide comprises more than one influenza virus surface protein peptide and each respective influenza virus surface protein peptide is separated from an adjacent influenza virus surface protein peptide by a spacer.

As used herein, as will be apparent to those of skill in the art, "spacer" refers to non-native peptide sequence that is positioned between two different, for example, non-contiguous peptide sequences. Specifically, the spacer or linker is provided so that the two different peptide sequences are capable of or are arranged to fold independently. In some embodiments, the spacer is preferably selected so that the spacer acts as a flexible linking sequence between the two peptides. Examples of suitable spacers are provided herein; however, other suitable spacers will be readily apparent to one of skill in the art and are within the scope of the invention.

According to another aspect of the invention, there is provided a method of eliciting an immune response against an influenza virus surface protein comprising: preparing a fusion protein comprising a Filoviridae Virus glycoprotein comprising an influenza surface protein peptide inserted in the mucin-like domain of the Filoviridae Virus glycoprotein wherein the influenza virus surface protein is selected from the group consisting of hemagglutinin and matrix-2 and the influenza virus surface protein peptide comprises 6 or more consecutive amino acids of the influenza virus surface protein sequence;
assembling virus-like particles comprising the fusion protein; and
immunizing an individual in need of immunization against influenza virus with an effective amount of the virus-like particles.

In some embodiments, the fusion peptide comprises more than one influenza virus surface protein peptide and each respective influenza virus surface protein peptide is separated from an adjacent influenza virus surface protein peptide by a spacer.

As will be appreciated by one of skill in the art, the immune response generated by the fusion protein may be increased or enhanced over the immune response that would be generated in a control individual, that is, an individual of similar age or condition as the immunized individual, immunized with the influenza virus surface protein alone.

As will be appreciated by one of skill in the art, as used herein, "an effective amount" of the fusion peptide or a virus-like particle comprising the fusion peptide is an amount that is sufficient to elicit an immune response. Such an effective amount will depend on several factors, for example, the age, weight and general condition of the individual. Methods for determining such an effective amount will be readily apparent to one of skill in the art and/or easily determined through routine experimentation.

In some embodiments of the invention, the fusion peptide comprises the amino acid sequence as set forth in SEQ ID No:1, SEQ ID No:2 or SEQ ID No. 3, as set forth below.

(SEQ ID NO: 1)
GPGPGEKTHNGKLCDLDGVKPLILRDCSVAGWLLGNPMCDEFINVPEWS

YIVEKANPANDLCYPGNGPGPGCYPGYFADYEELREQLSSVSSFERFEI

FPKESSWPNHTVTGPGPGEKEVLVLWGVHHPSNIGPGPGPKVRDQEGRI

NYYWTLLEPGDTIIFEANGNLIAPWYAFALSGPGPGNNEKFDKLYIWGV

HHPGTDSDQISLYAQASGRITVSTKRSQQTVIPNIGSRPRVRDVSSRIS

IYWTIVKPGDILLINSTGNLIAPRGYFKIRSGPGPG (SEQ ID NO: 2)
GPGPSAEQVDTIMEKNVTVTHAQDILEKTHGSAINSSMPFHNIHPLTIG

ECPKYVKSNRLVLATGLRNSPGSASLLTEVETPIRNEWGCRCNGSASTQ

KAIDGVTNKVNSIIDKMNTQFEAVGREFNNLERRIENLNKKMEDGFLDV

WTYNAELLVLMENERTLDFHDSNVKNLYDKVRRQLRDNAKELGNGSA (SEQ ID NO: 3)
GGSSLLTEVETPIRNEWGCRCNDSSDGGGSSLLTEVETPTRNGWECKCS

DSSDGGGSSLLTEVETPIRNEWGCRCNDSSDGGGSSLLTEVETPIRNGW

ECRCNDSSDGGGS

Thus, in this study, we have generated three fusion proteins, EboGPΔM-tetrameric M2e (tM2e), EboGPΔM-HAcsM2e, and EboGPΔM-HA$_{H5-1}$-3, incorporated these fusion proteins into VLPs and expressed them in VSV vector aimed to induce strong and broadly neutralizing antibodies against various strains of influenza virus.

SEQ ID No:1 is the amino acid sequence of the EboGPΔM-HA$_{H5-1-3}$ fusion peptide. As can be seen, the peptides comprising head regions from H5, H1 and H3 are separated by a "GPGPG" spacer. As will be appreciated by one of skill in the art, insertion of a spacer between each peptide enhances the exposure of each peptide, and prevents the undesirable "hold" or "hiding" of domain or epitopes of the peptides. Suitable spacers or linkers include but are by no means limited to glycine-proline-glycine-proline-glycine (GPGPG), glycine-serine-alanine (GSA) and glycine-glycine-serine (GGGS) linkers (11, 41), or other linkers (GSA) (42).

As discussed above, there are at least 18 different subtypes of hemagglutinin.

Depending on the particular situation, for example, the animal(s) being immunized and/or the identity of circulating influenza strains, different hemagglutinin head domains may be used in other embodiments. Furthermore, as discussed herein, shorter sequences of the head domain and/or one, two, three or more head domain peptides may be inserted into the mucin-like domain.

SEQ ID No:2 corresponds to the amino acid sequence for the fusion peptide EboGPΔM-HAcsM2e. Specifically, the peptides corresponding to the conserved region of hemagglutinin and the M2 peptide are separated by a spacer. In this embodiment, the spacer is GSA, although any suitable spacer, for example, GPGPG or GGGS, may be used instead.

As will be appreciated by one of skill in the art and as discussed above, peptides of different lengths derived from regions of hemagglutinin and/or the M2 peptide may be inserted into the mucin-like domain and are within the scope of the invention.

SEQ ID No: 3 corresponds to the amino acid sequence for EboGPΔM-tM2e, that is, M2e peptides taken from influenza viruses capable of infecting human, birds and swine. In this embodiment, the sequence of peptides is human/birds/human/swine. As will be appreciated by one of skill in the art, M2e sequences from other influenza viruses and/or other combinations thereof may be used within the invention, as discussed above. As discussed above, these two conserved regions are separated by a spacer. In this embodiment, the spacer is GPGPG, although any suitable spacer, for example, GSA or GGGS, may be used instead.

In these embodiments, the MLD domain from 305 aa to 483 aa was deleted. As discussed herein, it is of note that other suitable tolerated deletions of the MLD domain may be used or alternatively the influenza surface proteins may be inserted in frame into the MLD. As will be apparent to one of skill in the art, a variety of fusion peptides have been demonstrated to provide enhanced immunity, as discussed herein. It is of note that immunizing or vaccinating individuals with one of more fusion peptides and/or VLPs comprising the fusion peptides of the invention will provide better immunity.

As will be apparent to one of skill in the art, this represents one example of a tolerated deletion of the mucin-like domain as the resulting fusion protein remains capable of presenting the inserting peptides to the individual's immune system as discussed above. Other suitable tolerated deletions will be readily apparent to one of skill in the art and/or can be determined through routine experimentation.

As discussed above, the development of influenza A virus universal vaccine is a major focus for the eradication of influenza virus infection. However, this has been very challenging due to the mutation rate in the influenza A virus. Although the conserved region of Hemagglutinin (HA) and Matrix 2 (M2) protein are very promising for the development of influenza vaccine, studies have shown that the immune response induced by using the conserved peptides alone is not strong enough and cannot clear the viral load in the lungs. Thus, there is a need to produce stronger immune responses against these conserved epitopes to develop a functional universal vaccine against Influenza A virus. As discussed herein, it has been found that by targeting the conserved epitopes to the dendritic cells (DCs) it is possible to stimulate more efficient innate and adaptive immune responses. We have recently developed a novel DC-targeting vaccine platform using Ebola glycoprotein (EboGP) DC-targeting domain-based fusion protein technology. Here, we will use this technology to generate universal vaccines against Influenza A by fusing a DC-targeting/activation domain (EboGPΔM), derived from EboGP to I) a tetrameric conserved extracellular domain of M2 (M2e) of Influenza A strains from human, birds, and swine (FIGS. 1B and C); 2) the conserved stalk regions (HAcs) of HA and an M2 polypeptide from H5N1 strain (FIGS. 1A and C); 3) the HA head regions polypeptides ($HA_{H5-1-3}$) derived from H5N1, H1N1 and H3N2 strains (FIG. 1C). These constructed fusion proteins-expressing plasmids are named as EboGPΔM-tM2e, EboGPΔM-HAcsM2e, and EboGPΔM-$HA_{H5-1-3}$ (FIG. 2A).

Figure 3:
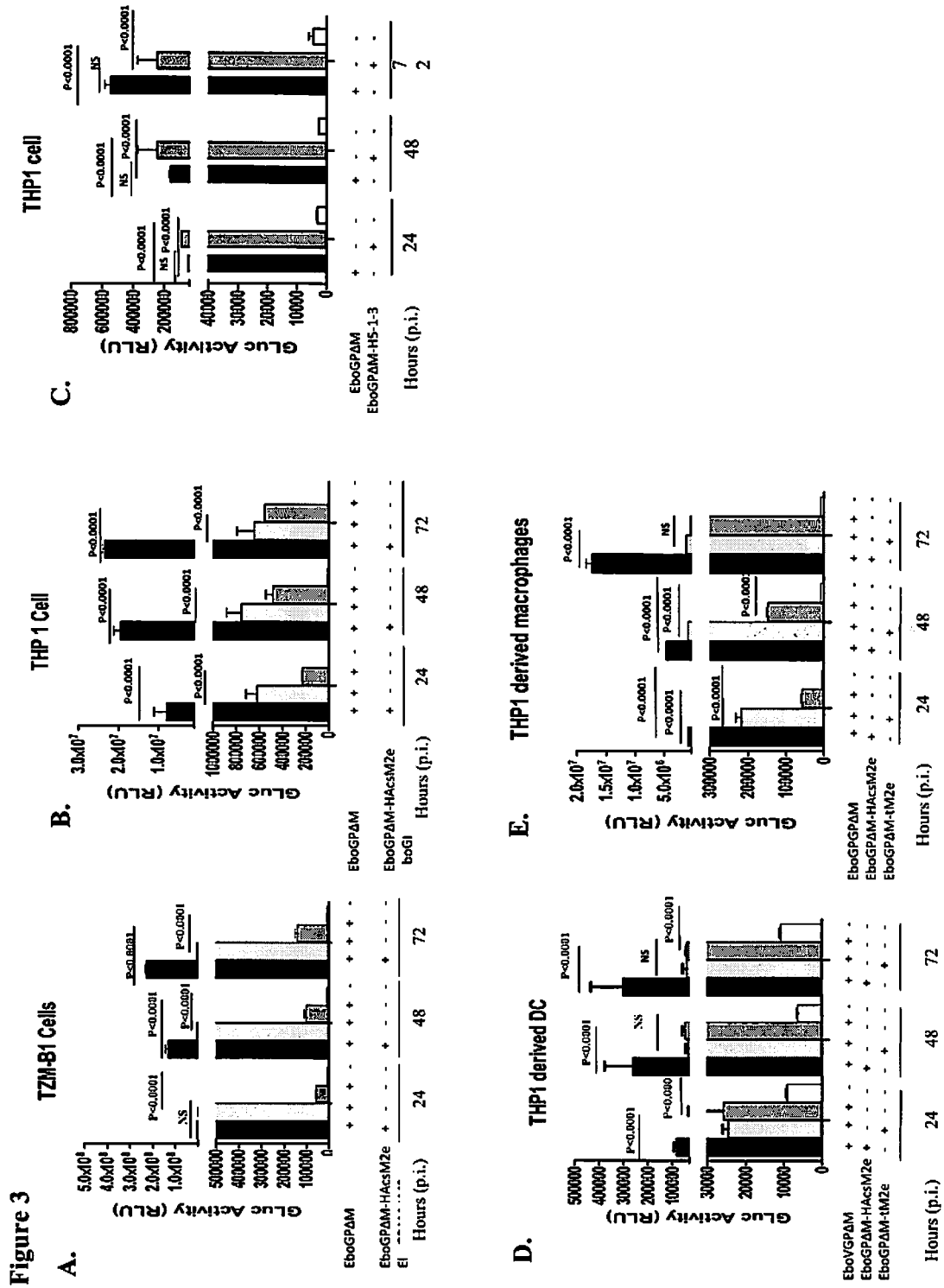
FIG. 3: Investigation of cell entry ability of EboGPΔM-HA$_{H5-1-3-}$, EboGPΔM-HAcsM2e- and EboGPΔM-tM2e-pseudotyped VLPs. Various types of cells, including TZMB1 cells (A), THP1 (B and C), THP1 differentiated DCs (D) and macrophages (E) were infected by equal amounts of each of EboGPΔM-tM2e- and EboGPΔM-HAcsM2e-, EboGPΔM- and native influenza HA/NA/M2-pseudotyped VLPs (adjusted with equal amount of HIV p24). At different time intervals as indicated, the supernatants from the infected cell cultures were collected and subjected to GLuc activity assay. The data were done in triplicate.
Figure 4:
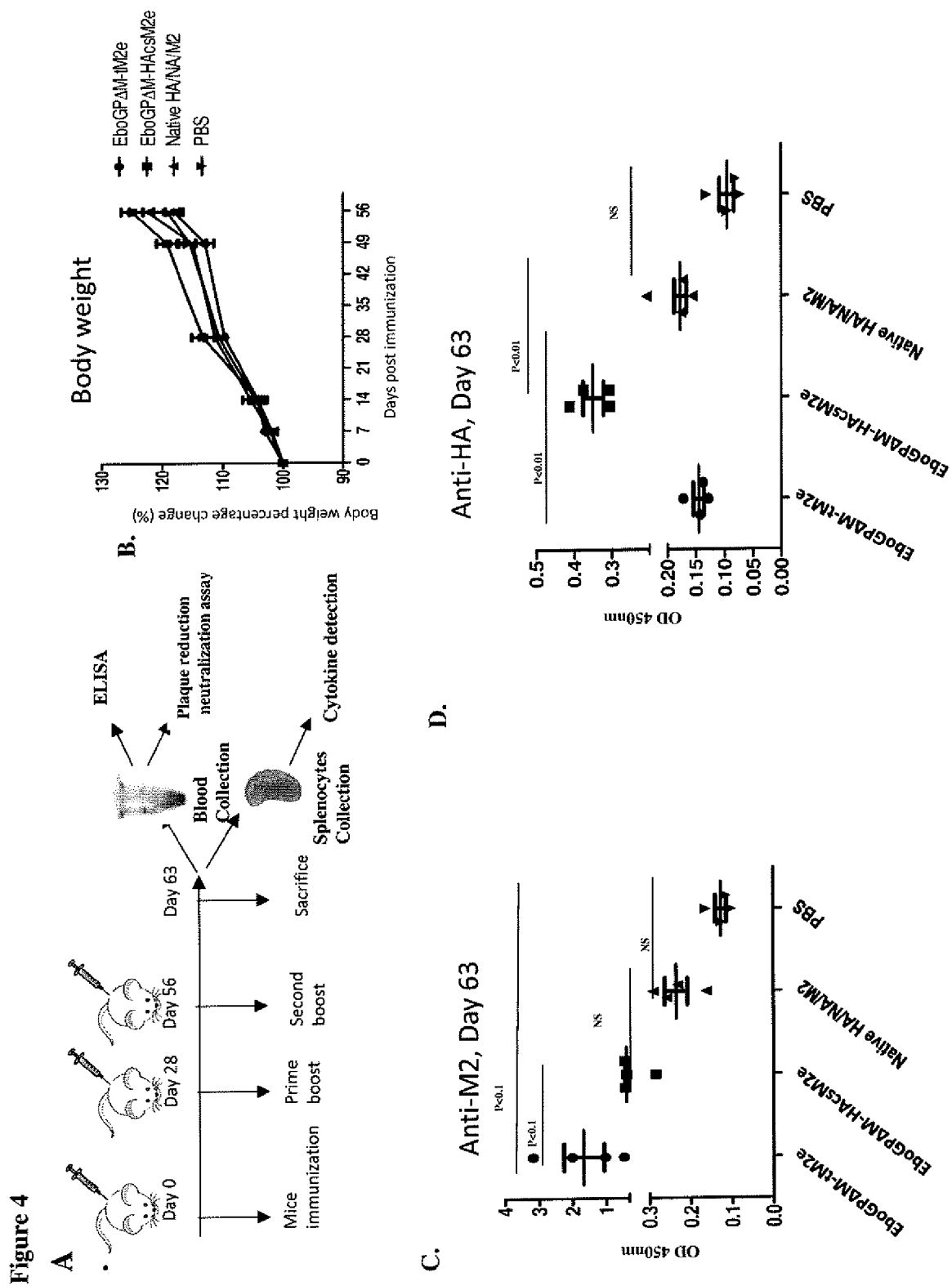
FIG. 4: The immunization of EboGPΔM-HAcsM2e- and EboGPΔM-tM2e-pseudotyped VLPs induced significantly higher specific anti-HA and M2 antibodies than native influenza HA/NA/M2-VLPs in BALB/c mice. A) Schematic of different pseudotyped VLPs immunization protocol used in this study. The BALB/c mice were injected subcutaneously with 100 ng of different pseudotyped VLPs, as indicated, at day 0, 28 and 56. At days 7, Day 35, and Day 63 after the immunization, the blood from immunized mice was collected and on 63 days of post-immunization, the splenocytes were harvested. B) Mice body weights were monitored weekly in which 100% body weight was set at day 0. The levels of anti-M2 (C) anti-HA (D) antibodies in the sera of immunized mice were detected by corresponding ELISAs. Statistical significance was determined using an unpaired t-test, and significant p values were shown as P≥0.001 or P≥0.01.

As will be appreciated by one of skill in the art, it is possible that some configuration of inserted large peptides could interrupt EboGPΔM's ability to target DCs. To test if these fusion proteins are still able to target DCs/macrophages, we have produced each EboGPΔM-fusion protein-pseudotyped HIV virus-like particles (VLPs) and investigated their abilities to target DCs/macrophages (FIG. 2B). As discussed below, results revealed that all EboGPΔM-fusion protein were able to deliver VLPs into DCs and macrophages (FIG. 3). We further investigated whether EboGPΔM-HAcsM2e or EbovGPΔM-tM2e pseudotyped VLPs could elicit immune responses against influenza in mice and the results showed a significantly stronger M2 and HA-specific humoral immune responses, as compared to native HA, NA, and M2 incorporated VLPs (FIG. 4).

As discussed herein, the fact that the humoral immune response as compared to the native peptides, including elevated production of IFN-γ and RANTs, IL-6 and IL-10, indicates that the enhancement of the immune response is surprisingly more robust and varied than immunizing with a native form of HA, NA, and M2 incorporated into VLPs. Furthermore, it is also important to note that these data are from in vivo experiments.

Figure 5:
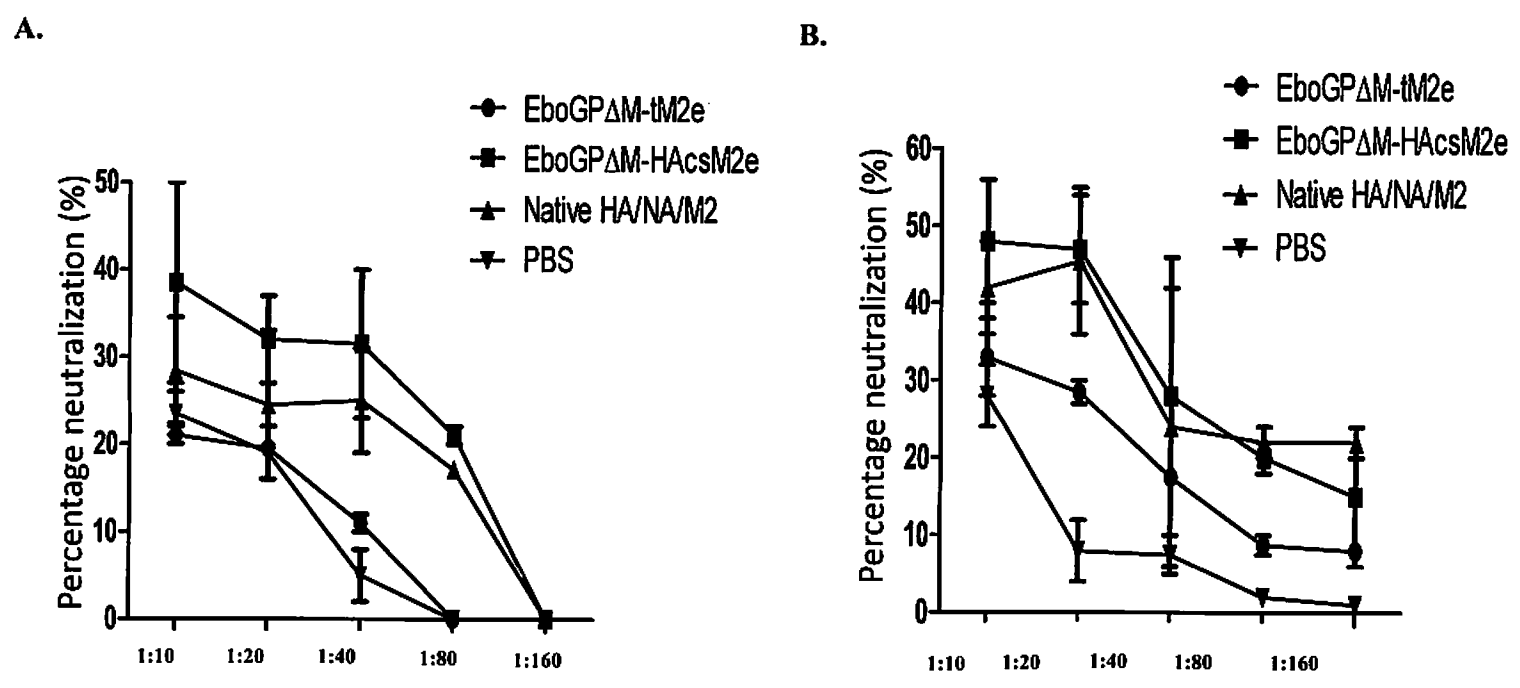
Figure 6:
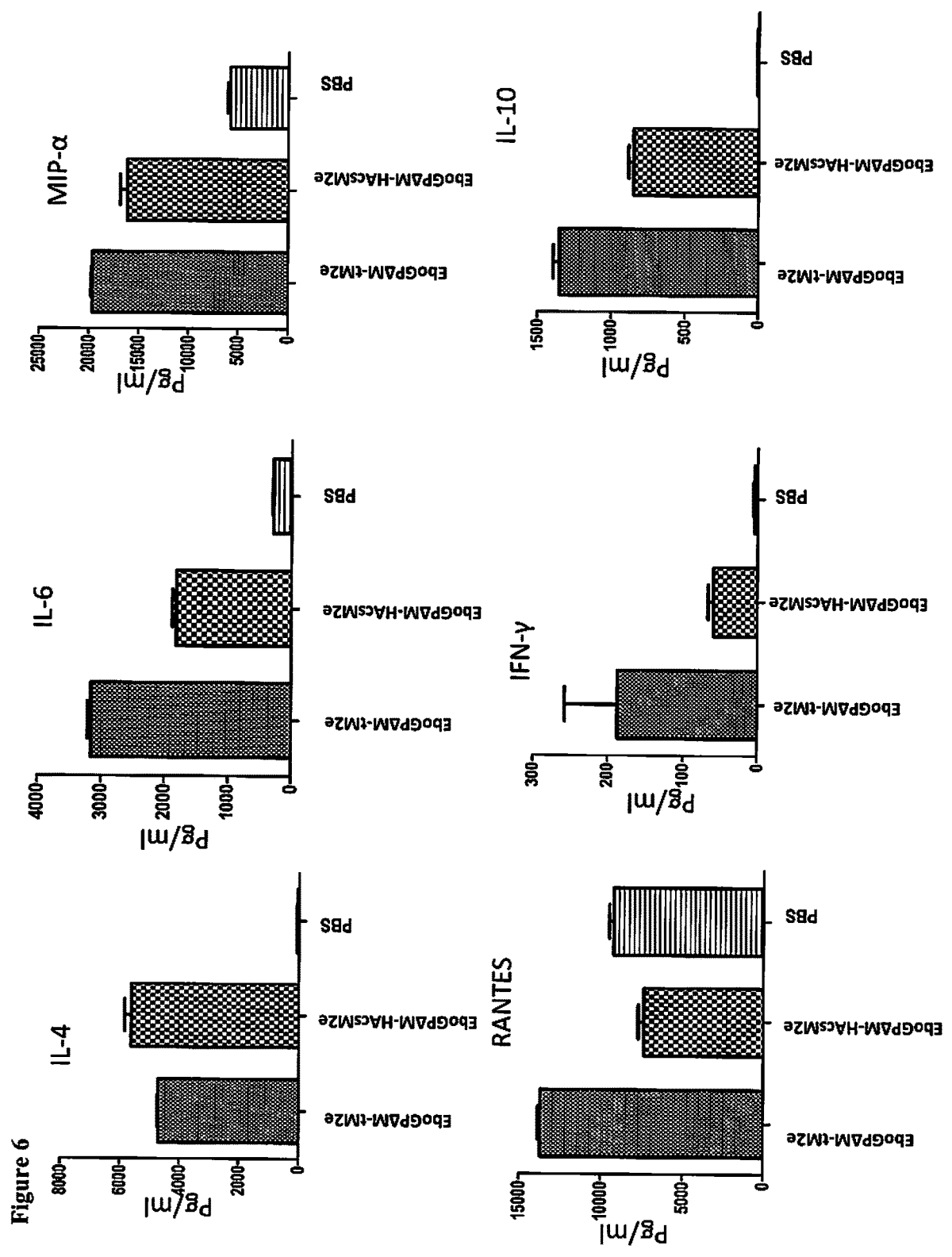

Also, the vaccine-induced neutralization against the wild type influenza challenge was investigated, and data revealed that the serum from EboGPΔM-HAcsM2e-immunized mice exhibited a modestly more effective neutralization activity against the wild type influenza (FIG. 5), as discussed below. Moreover, our analyses revealed that significantly higher levels of IL-6, RANTES, and IFN-γ were produced when splenocytes from mice immunized by EbovGPΔM-tM2e stimulated with M2e peptides (FIG. 6). Collectively, this study gives evidence for the first time the new influenza A virus universal vaccine that combines a DC-targeting/transmember domain derived from EboGP with influenza A conserved polypeptides derived from viral HA and M2 proteins. This study demonstrates that enhancement of DC-targeting and immunogenicity of influenza HA/M2 conserved regions is able to induce more potent protective immunity against various subtypes of influenza infection. Since the VSV-EboGP vaccine has been proved to be safe and protective efficacy against EBOV in human clinical trials (1, 17), our vaccine approach will provide a new prophylactic vaccine against various strains and subtypes of influenza infections.

Despite the progress made in the development of a universal vaccine for influenza viral infection having clinical trials at phase I, II and III clinical trials (40), there is still no universal vaccine endorsed for the treatment of influenza viral infection. The development of a universal vaccine against influenza virus remains the most prioritized recommendation from the Center for Disease Control for the management of influenza viral infection. (16). Recently, attention has been shifted to targeting of DCs/macrophages for the development of vaccine due to its tendency to induce strong immune responses (25) is being used for the development of vaccines against adenovirus (8), yellow fever (31), and cancer (5) among others.

We obtained strong immune responses by targeting the DCs/macrophages using EboGP to elicit immune responses. Since the EboGP also has an affinity for DCs/macrophages (4, 23), and its mucin-like domain can be removed without affecting the DCs targeting ability of EBOV GP (22, 24), we have developed a highly efficient DC-targeting vaccination technology. With this new technology, the MDDC/MDM-targeting domain and the transmembrane region of EboGP (EboGPΔM) have been fused with various large heterologous polypeptide (up to 241 aa). This fusion strategy can significantly facilitate the delivery of large polypeptides into APCs and significantly promote immune responses against the antigens. In this study we have placed the conserved influenza M2e or the conserved stalk regions or large polypeptides derived from head regions of subtypes H5, H1 and H3 into EboGPΔM (FIG. 1C). Since the influenza HA stalk and conserved M2 are highly conserved in almost all strains of influenza virus, and it is much less affected by either the mutation or the reassortment that is peculiar to the influenza virus, the fusions of influenza HA stalk and conserved M2 with EBOGPAM elicit a broad protection against all strains of influenza virus be they presently circulating strains or future strains.

To achieve this, we have produced EboGPΔM-tM2e-, EboGPΔM-HAcsM2e-, and EboGPΔM-HA$_{H5\text{-}1\text{-}3}$-pseudotyped VLPs and further investigated whether the infusion of influenza antigenic polypeptides will not impede that cell entry of EboGPΔM into the DCs and macrophages. The data indicate that all of EboGPΔM-tM2e-, EboGPΔM-HAcsM2e-, and EboGPΔM-HA$_{H5\text{-}1\text{-}3}$-pseudotyped VLPs were able to infect TZMB-1 cells, THP-1 cells, THP-1 differentiated macrophages, and THP-1 differentiated DCs (FIG. 3A-E) efficiently. These observations provide evidence for the efficiency of the highly conserved influenza M2e, the stalk regions, or large polypeptides derived from head regions of H5, H1 and H3 to be delivered into DCs and macrophages in the presence of EboGPΔM.

In this study, we further analyzed EboGPΔM-tM2e-, EboGPΔM-HAcsM2e-pseudotyped VLPs for their immunogenicity ability as compared to that of the VLPs-incorporated with native HA/NA/M2. The anti-M2 response induced by EboGPΔM-tM2e was more robust than EbovG-PAMuc-HAcsM2e and native HA/NA/M2-VLPs. The superiority of anti-M2 immune responses observed by EboGPΔM-tM2e is expected because, in the construction of plasmid, EboGPΔM-tM2e has four copies of M2e while EboGPΔM-HAcsM2e has just only one copy. Also, these results suggest that the fusion of EboGPΔM with influenza M2e facilitated the induction of anti-M2 immune responses since EboGPΔM-tM2e induced highly robust and significantly different anti-M2 immune response than native HA/NA/M2 VLPs. While not wishing to be bound to a particular theory or hypothesis, this may be due to two mechanisms: 1) the EboGPΔM-tM2e fusion protein contains four copies of M2e peptides, and 2) the EboGPΔM-tM2e fusion protein are able to enter into DCs/macrophages efficiently, which is very important to induce robust immune responses. Some reports have shown that four copies of M2e in a recombinant protein used for immunization displayed induced robust anti-M2 immune responses using flagellin as an adjuvant (36). Although their study did not compare the anti-M2 immune responses of high copies of M2 with a lower number of copies of M2, our study showed that the number of copies of M2 might account for the various titers of anti-M2 antibody-induced.

Another observation was that EboGPΔM-HAcsM2e-pseudotyped VLPs induced significantly stronger anti-HA immune responses than the native HA/NA/M2-VLPs. Since the influenza HA used in our study was obtained from H5N1, we used both recombinant HA (rHA) and HA2 peptide to coat the plate respectively for ELISA.

Although the anti-HA immune response induced by EboGPΔM-HAcsM2e-VLPs was more than native HA/NA/M2-VLP when HA2 peptides-coated plate used in ELISA, there was no statistically significant difference using rHA-coated ELISA. Thus, the stimulated immune response against HA2 antigens was made stronger by the presence of EboGPΔM-HAcsM2e.

influenza HA stalk has been previously described to induce broadly neutralizing antibodies by relying on Fc-Fcγ receptor interaction for protection in vivo (26). We investigated whether the sera from mice immunized with EboGPΔM-HAcsM2e will have a significant difference in the neutralization effect compared with other groups. Indeed, the immunization with EboGPΔM-HAcsM2 induced more potent neutralizing effect against influenza H1N1 strain than that of native HA/NA/M2-VLPs and EboGPΔM-tM2e (FIG. 5). This higher level of neutralization might be attributed to a more efficient DC-targeting of HAcs and consequently induced higher levels of anti-HA2 antibodies. Also, as expected the sera from mice immunized with EboGPΔM-tM2e did not exhibit neutralizing activity since antibodies against M2e majorly mediate antibody-dependent cellular cytotoxicity (ADCC), which can not be monitored in our experimental system.

With the establishment of the stimulation of stronger humoral immune responses by the infusion of EboGPΔM with tM2e or HAcsM2e, we further investigated if this infusion can also induce cellular immune responses. Our results revealed that the M2e-specific cellular responses, including elevated productions of IFN-γ and RANTs, IL-6 and IL-10, were also enhanced significantly in the groups of mice immunized with EboGPΔM-tM2e, compared with EboGPΔM-HAcsM2 and PBS (FIG. 6). These data EboGPΔM-tM2e can not only induce more efficient antibody response, but also facilitate cellular responses against M2e. As will be known to those of skill in the art, the cytokines secreted have been associated with many biological functions and can protect against influenza virus infection (27). As discussed herein, this represents a surprising and unexpected benefit of targeting the influenza virus surface protein peptides to dendritic cells.

The enhanced influenza immune responses, and stronger neutralizing antibodies induced by EboGPΔM-HAcsM2 and/or EboGPΔM-tM2e provide evidence that EboGPΔM can enhance influenza-specific immunity by targeting DCs and have been developed as a novel DC-based vaccine strategy. In all, this study has shown for the first time that the infusion of influenza HA stalk or head regions, and conserved M2 with EboGPΔM can elicit stronger influenza immune responses that provide more effective protection against various strains of influenza virus. This efficient DC-targeting vaccination technology fusing with influenza conserved M2e, the conserved stalk regions or large polypeptides derived from head regions of H5, H1 and H3 provides a universal vaccine against influenza virus and will possibly put an end to the annual formulation of vaccine and fear of evolution of a pandemic strain of influenza virus infection.

The novelty of this study lies in the use of Ebola glycoprotein (EboGP) DC-targeting domain-based fusion protein technology to fuse with the conserved M2e and/or the conserved stalk regions (HAcs) or HA head regions polypeptides (HA$_{H5\text{-}1\text{-}3}$) derived from subtypes H5, H1 and H3 to generate universal vaccines against Influenza A. The rationale of fusion strategy is to enhance their DCs/macrophages targeting, thereby significantly facilitate both innate and adaptive immune responses. Indeed, immunization of EboGPΔM-HAcsM2e and EboGPΔM-tM2e-pseudotyped VLPs induced much more efficient humoral and cellular immune responses. More importantly, EboGPΔM-HAcsM2e-VLP also elicited neutralizing antibodies stronger than native HA/NA/M2-VLPs against different strains of influenza strains suggesting its tendency to be used in the development of a universal vaccine for influenza virus.

The invention will now be further elucidated and/or described by way of examples; however, the invention is not necessarily limited to or by the examples.

EXAMPLE 1. Generation of EboGPΔM-HAcsM2e, EboGPΔM-tM2e, and EboGPΔM-HA$_{H5\text{-}1\text{-}3}$ Fusion Proteins and Investigation of their DC/Macrophage-Targeting Abilities To develop universal influenza vaccine, we have chosen and synthesized the conserved regions in the head or stalk regions of HA, and the conserved extracellular domain of Matrix 2 (M2e) proteins of Influenza A strains from human, birds, and swine (FIG. 1B). The tetrameric M2e polypeptide comprised of two copies of the conserved extracellular domain (24 aa) from human influenza M2, one copy of the extracellular domain (24 aa) from avian influenza and one copy from or swine influenza M2 protein (FIG. 1C) (21). The conserved stalk regions (HAcs) of hemagglutinin (HA) was derived from influenza H5N1, and polypeptides (HA$_{H5-1-3}$) were selected from the HA head regions from H5N1, H1N1 and H3N2 strains (FIGS. 1b and c). After being synthesized, each sequence was in frame inserted into an EboGPΔM expressing plasmid (49), pCAGG-EboGPΔM, and the resulted fusion protein-expressing plasmids are named as pCAGG-EboGPΔM-tM2e, pCAGG-EboGPΔM-HAcsM2e, and pCAGG-EboGPΔM-HA$_{H5-1-3}$ (FIG. 2A).

In an attempt to test the expression of these fusion proteins and if they can still target DCs/macrophages, we produced each EboGPΔM-fusion protein-pseudotyped HIV VLPs. We co-transfected each of pCAGG-EboGPΔM-tM2e, pCAGG-EboGPΔM-HAcsM2e, and pCAGG-EboGPΔM-HA$_{H5-1-3}$ with a HIV Gag/Pol expression plasmid (CMV-Gag/Pol) and HIV vector (ΔRI/ΔE/Gluc) containing a secreted Gaussia luciferase (Glu) gene replaced on nef position, as previously described (2), which was used to monitor the ability of the VLPs to target the DCs/macrophages, into a HEK 293T cells (FIG. 2B). After 48 hours of transfection, the produced VLPs were collected from the supernatant by ultracentrifugation. Meanwhile, a native influenza HA, NA and M2 plasmids (native HA/NA/M2) pseudotyped VLPs were produced using the same procedure as described previously (3). The presence of each of EboGPΔM-tM2e, EboGPΔM-HAcsM2e, or EboGPΔM-HA$_{H5-1-3}$ fusion proteins was checked by western blot (WB) with corresponding antibodies (FIG. 2c-e). The WB results revealed the EboGPΔM-tM2e, EboGPΔM-HAcsM2e, or EboGPΔM-HA$_{H5-1-3}$ fusion proteins were well expressed in the transfected cells and incorporated into VLPs, while EboGPΔM-HAcsM2e fusion protein, and native HA in Native HA/Na/M2 VLPs were detected (FIGS. 1D and E, Lanes 1 and 2) and the EboGPΔM-HAcsM2e and EboGPΔM-tM2e fusions were detected with anti-M2 antibody WB (FIGS. 1D and E, Lanes 1 and 4).

To evaluate cell targeting abilities, an equal amount of EboGPΔM-tM2e, EboGPΔM-HAcsM2e-, or EboGPΔM-HA$_{H5-1-3}$-pseudotyped Gluc$_+$-VLPs (adjusted with HIV p24 levels) were used to infect HEK 293T cell, TZ-MB1 cells, THP1 cell, THP1 differentiated DCs, THP1 differentiated macrophages, human MDMs, and MDDCs. Since the VLPs encoding gene for GLuc protein which will be expressed and released at subsequent replication of the particles, the entry ability of the infused VLPs was monitored by detecting this GLuc activity in the respective cell culture medium by collecting the supernatant for 3 days for all the cells except for, human MDMs, and MDDCs which was observed for 8 days. The results revealed that the fusion of EboGPΔM with influenza HAcsM2e, tM2e or HA$_{H5-1-3}$ did not impede the cell entry efficiency of the pseudotyped-VLPs in various cell lines and THP1 differentiated DCs, THP1 differentiated macrophages and DCs (FIG. 3A-E) and interestingly, EboGPΔM-tM2e, EboGPΔM-HAcsM2e had better entry efficiency compared to EboGPΔMuc in HEK 293T cells suggesting that the fusion of EboGPΔM with influenza HA and/or M2 can aid the cell entry efficiency of EboGPΔM. The mechanism for the binding ability of the pseudotyped-VLPs is not clear. Overall, these results demonstrated that the fusion of EboGPΔM with polypeptides derived from influenza HA or M2 does not impede the DCs and macrophages cell targeting ability.

EXAMPLE 2. The EboGPΔM-tM2e- and EboGPΔM-HAcsM2e-Pseudotyped HIV VLPs Induced Significantly Higher Anti-Influenza HA and M2 Antibodies than Native Influenza HA/NA/M2-VLPs in Mice, Respectively Since EboGPΔM-tM2e- and EboGPΔM-HAcsM2e-VLPs can efficiently enter DCs and macrophages, we next investigated whether the EboGPΔM-tM2e- and EboGPΔM-HAcsM2e-VLPs could efficiently stimulate influenza HA and M2 immunogenicity in vivo. The Balb/c mice were immunized with 100 ng of EboGPΔM-tM2e-, EboGPΔM-HAcsM2e-, the native HA/NA/M2-VLPs or PBS and boosted at days 28 and 56 with same amounts of VLPs, as shown in FIG. 4A. At days 0, 28 and 56 while the body weights for all mice immunized were monitored. A slight increase was observed in the bodyweight of all the groups of mice immunized with no statistically significant difference (FIG. 4B). At day 63 of post-immunization, sera from mice were collected as described in Materials and Methods, and both anti-HA and anti-M2 humoral responses were determined by ELISA. As observed in FIGS. 4C and D, influenza M2-specific humoral immune responses against influenza M2 were detected in mice injected with EboGPΔM-tM2e- and EboGPΔM-HAcsM2e-, native HA/NA/M2-VLPs, while influenza HA-specific humoral responses were detected in EboGPΔM-HAcsM2, and native HA/NA/M2-VLPs-immunized mice, but not in EboGPΔM-tM2e-immunized mice (FIG. 4D). Interestingly, our results revealed that the influenza M2-specific antibody titers for the group of mice immunized with EboGPΔM-tM2e VLPs were significantly higher than native HA/NA/M2-VLPs. Also, HA-specific antibody titers in the group of mice immunized with EboGPΔM-HAcsM2e-VLPs were substantially higher than native HA/NA/M2-VLPs. We are also in the process of testing immunogenicity of EboGPΔM-HA$_{H5-1-3}$-pseudotyped VLPs in mice. Overall, our results demonstrated that immunization either with EboGPΔM-tM2e or EboGPΔM-HAcsM2e-VLPs can elicit significantly stronger anti-influenza HA or anti-M2 antibody responses than that with a native HA/NA/M2-VLPs respectively in the mice.

EXAMPLE 3. Antibodies Induced in Immunized Mice by EboGPΔM-HAcsM2e Partially Inhibited H1N1 Influenza Virus Infection Antibodies raised against influenza HA have been demonstrated to inhibit the infection of influenza virus in cells (14, 15). We investigated if the antibodies in sera of the mice immunized by EboGPΔM-HAcsM2e or EboGPΔM-tM2e can neutralize influenza virus infection in vitro. For this purpose, we have chosen H1N1 (PR8 strain) influenza virus for this study. The virus (25 PFU/ml or 50 PFU/ml) were incubated with immunized mice sera for 1 hr at 37° C., and serum/viral mixtures were used to infect MDCK cells, incubated for 1 hour at 37° C., then covered with 0.8% Avicel and incubated at 35° C. and 5% C02 for 72 hours, fixed with 2% formaldehyde for 30 minutes, stained with crystal violet, washed and calculated the viral titer in the plaque forming unit per ml (PFU/ml), as described in Materials and Methods. The results revealed that sera from the mice immunized with EboGPΔM-HAcsM2e were able to modestly inhibit the H1N1 infection in a dose-dependent manner (FIG. 5). The sera dilution that achieved a 50% neutralization titer (NT$_{50}$) in the mice sera immunized with EboGPΔM-HAcsM2e was higher than that of sera of immunized mice with native HA/NA/M2-VLPs against H1N1, while mice sera immunized with EboGPΔM-tM2e did not show any neutralizing activity against H1N1 (PR8 strain) influenza virus infection (FIGS. 5A and B).

EXAMPLE 4. EboGPΔM-tM2e-Pseudotyped HIV VLPs-Immunized Mice Induced Cytokines after the Splenocytes Stimulated with Influenza M2 Peptides In Vitro We next evaluated the cell-mediated immune responses against Influenza M2 peptides induced upon immunization of mice. To achieve this, we stimulated Splenocytes isolated from immunized BALB/c mice with influenza M2 peptide and quantified the produced cytokines and chemokines using 8-plex mouse cytokine kit (BioRad). Our results revealed that EboGPΔM-tM2e-VLPs-immunized mice splenocytes produced significantly higher levels of MIP-1a, IL-6, RANTES, IFN-γ and IL-10, as compared to EboGPΔM-HAcsM2e and PBS-treated mice splenocytes (FIG. 6).

Figure 7:
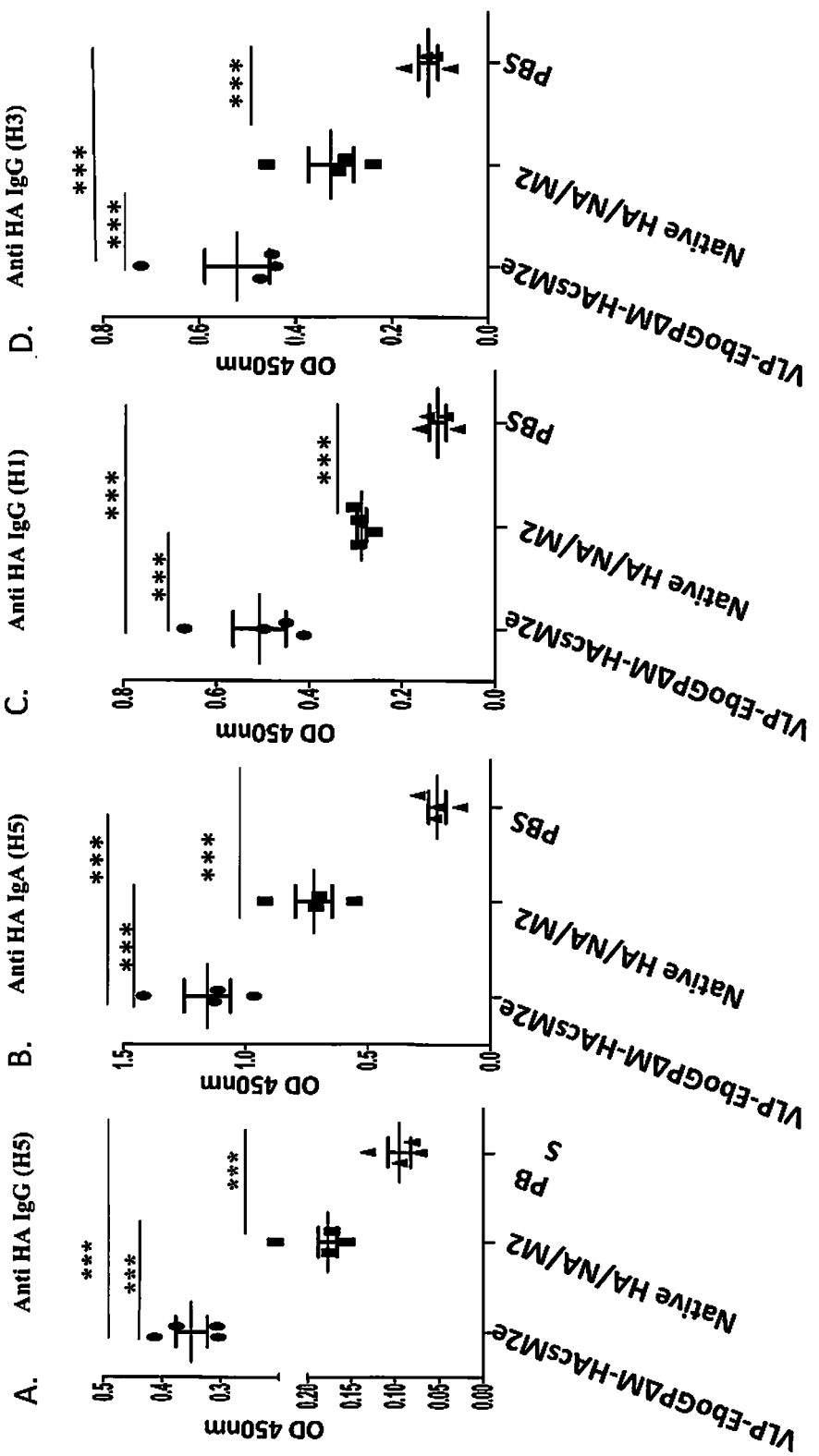
FIG. 7: VLP-EboGPΔM-HAcsM2e induced stronger anti-HA antibody responses against H5, H1 and H3 proteins than native HA/NA/M2 VLPs. The Balb/c mice were injected subcutaneously with 100 ng of VLP-EboGPΔM-HAcsM2eVLPs, Native HA/NA/M2 or PBS. Balb/c mice were immunized on Day 0 and boosted on Day 28. Blood was collected on day 35 after the immunization to investigate the anti-HA antibody-induced using ELISA. (A-B) A 96 well-plate was coated with 0.5 μg of HA recombinant protein from H5N1 overnight at 4° C. The HA antibody in the sera was detected using the ELISA technique, while anti-IgG and anti-IgA antibodies were used as secondary antibodies to detect either IgG or IgA HA antibodies in the sera. A 96 well-plate was coated with 0.5 µg of HA recombinant protein from (C) H1N1 or (D) H3N2 overnight at 4° C. The HA antibody in the sera was detected using the ELISA technique, using anti-IgG as a secondary antibody to detect IgG HA antibodies in the sera. Statistical significance was determined using an unpaired t-test, and significant p values were shown as P≥0.001 or P≥0.01.

EXAMPLE 5. VLP-EboGPΔM-HAcsM2e Induced Anti-HA Antibody Responses More than Native HA/NA/M2 VLPs in Mice Since EboGPΔM-HAcsM2e-VLPs can efficiently enter DCs and macrophages, we next investigated whether the EboGPΔM-HAcsM2e-VLPs could efficiently stimulate influenza HA immunogenicity in vivo. Balb/c mice were immunized on Days 0, 28 and 56. Blood was collected on day 63 after the immunization to investigate the anti-HA antibody-induced using ELISA. On day 63 of post-immunization, sera from mice were collected, and the anti-HA specific humoral responses were determined by ELISA. As observed in FIG. 7a-b, influenza anti-HA IgG, and IgA specific humoral immune responses against influenza H5N1 were detected in mice injected EboGPΔM-HAcsM2e- and native HA/NA/M2-VLPs. Interestingly, our results revealed that influenza (H5N1) HA-specific antibody titers for the group of mice immunized with EboGPΔM-HAcsM2-VLPs were substantially higher than native HA/NA/M2-VLPs. We also investigated if our vaccine candidate could induce immune responses against other strains of influenza. We therefore coated a 96 well plate with HA recombinant protein from H1N1 and H3N2. Surprisingly, the EboGPΔM-HAcsM2-VLP induced a significantly higher anti-IgG HA-specific immune response in mice than the native HA/NA/M2 (FIG. 7c-d). This result indicates that EboGPΔM-HAcsM2-VLP can induce broad immune responses against influenza virus strains.

Figure 8:
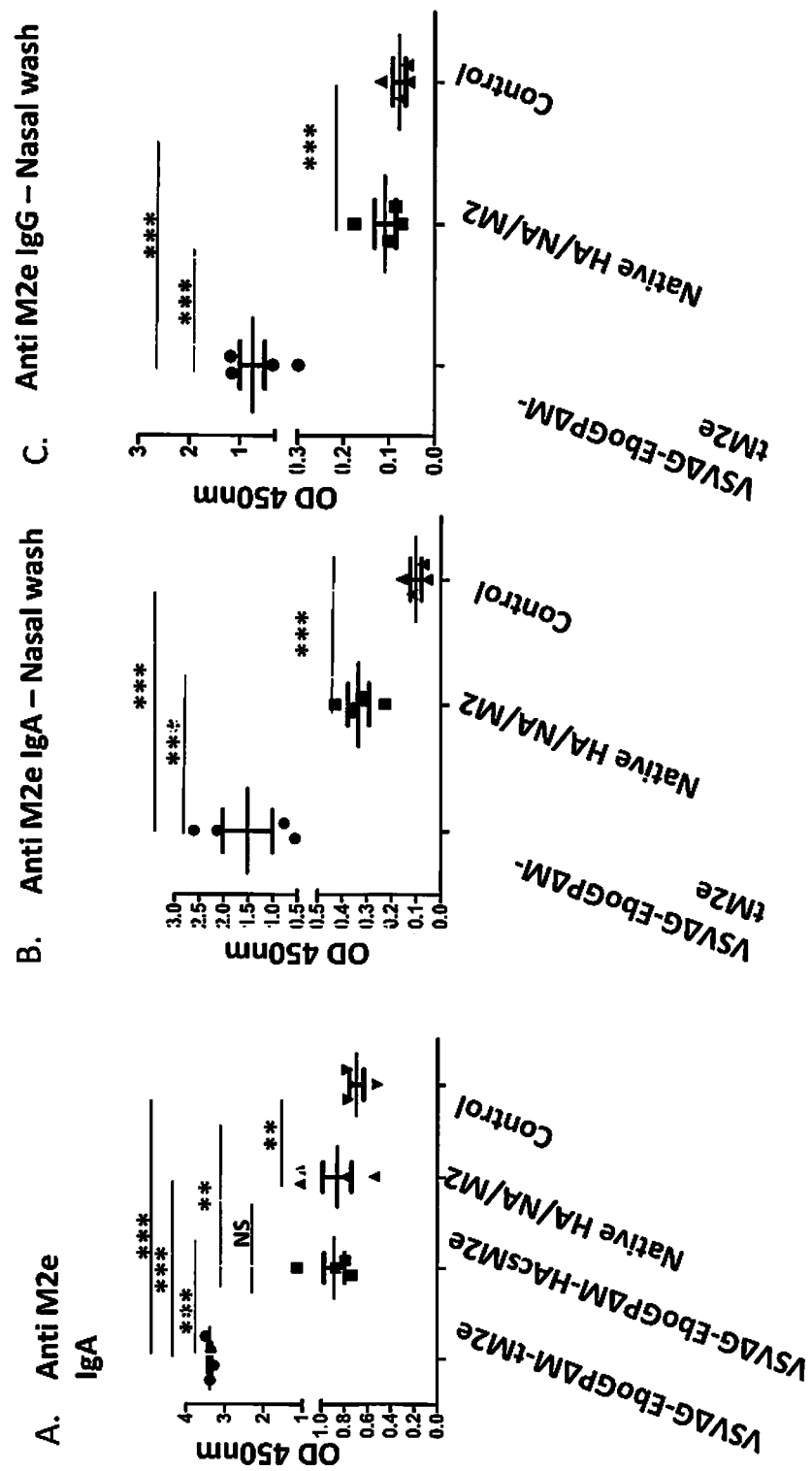
FIG. 8: Investigation of VSV-based EboGPΔM-tM2e vaccine-induced more potent immune responses against influenza M2 protein in Balb/c mice. The Balb/c mice were injected intramuscularly with Balb/c mice were immunized with a $1\times10^7$ tissue culture infectious dose of 50% (TCID$_{50}$) of the recombinant VSV virus expressing EboGPΔM-tM2e or EboGPΔM-HAcsM2e in the first week and prime boosted in the third week. Meanwhile, VLP of Native HA/NA/M2 or PBS was used as control. Blood and the nasal washes were collected on day 35 after the immunization to investigate the anti-HA antibody-induced using ELISA. (A) A 96 well-plate was coated with 1.0 µg of M2e peptide from H5N1 overnight at 4° C. The IgA M2e antibody in the sera was detected using the ELISA technique, using an anti-IgA secondary antibody. (B-C) The M2e IgA and IgG antibodies in the nasal wash were also detected using A 96 well-plate coated with 1.0 µg of M2e peptide from H5N1 overnight at 4° C. The HA antibody in the sera was detected using the ELISA technique, using anti-IgG as a secondary antibody to detect IgG HA antibodies in the sera. Statistical significance was determined using an unpaired t-test, and significant p values were shown as P≥0.001 or P≥0.01.

EXAMPLE 6. The VSV-Based Vaccine of EboGPΔM-tM2e Induced More Potent Immune Responses Against Influenza M2 Protein in Balb/c Mice A VSV-based vaccine has been demonstrated to be safe and effective. We therefore developed a VSV-based vaccine for influenza by deleting the Glycoprotein of VSV and incorporated our peptides to form rVSV-EboGPΔM-tM2e or rVSV-EboGPΔM-HAcsM2e-. We further investigated the ability of these vaccine candidates to induce immune responses in vivo. Balb/c mice were immunized on Days 0 and 28. Blood was collected on day 35 after the immunization to investigate the IgA anti-M2e-specific antibody immune response induced using the ELISA technique. On day 35 of post-immunization, sera and nasal wash from mice were collected, and the anti-M2e specific humoral responses were determined by ELISA. As observed in FIG. 8a, influenza anti-M2e IgA specific humoral immune responses against influenza detected in mice injected rVSV-EboGPΔM-tM2e was significantly robust than native HA/NA/M2-VLPs. Also, in FIG. 8b-c, our results revealed that influenza IgA and IgG M2e-specific antibody titers in the nasal wash of the group of mice immunized with rVSV-EboGPΔM-tM2e were substantially higher than the native HA/NA/M2-VLPs.

EXAMPLE 7. EboGPΔM-H5-1-3 VLP and rVSV-EboGPΔM-HAcsM2e Vaccine Induced a More Robust Anti-HA Antibody, Respectively Responses More than Native HA/NA/M2 VLPs To induce neutralization antibodies, we fuse conserved HA epitopes from the head of H3N2 and Computationally optimized Broadly Reactive Antigen (COBRA) of H1N1, H5N1. We also investigated its ability to target MDMs and MDDCs. Since they can successfully target the MDMs and MDDCs, we investigated their capability to induce immune responses in mice. Balb/c mice were immunized on Days 0 and 28. Blood was collected on day 35 after the immunization to investigate the IgG and IgA anti-HA-specific antibody immune response induced in the sera and nasal wash, respectively, using the ELISA technique. On day 35 of post-immunization, sera and nasal wash from mice were collected, and the anti-HA specific humoral response was determined by ELISA.

Figure 9:
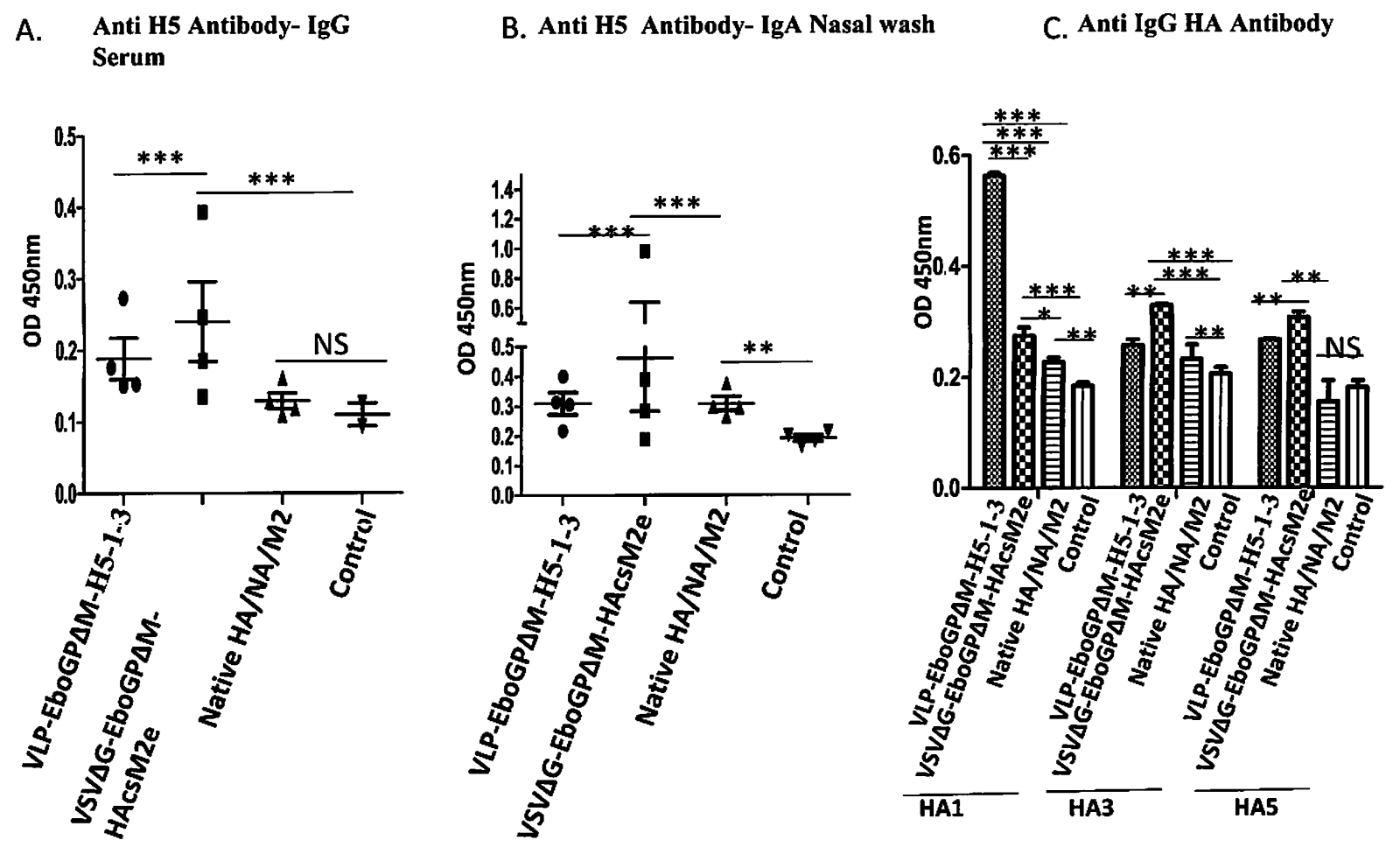

Interestingly, there was a high titer of anti HA antibodies in the sera and the nasal wash of the mice immunized with EboGPΔM-H5-1-3 VLP and rVSV-EboGPΔM-HAcsM2e than the native HA/NA/M2 VLP (FIG. 9a-b). We also investigated if the EboGPΔM-H5-1-3 VLP could induce anti-HA-specific immune responses against other strains of influenza. We found that both EboGPΔM-H5-1-3 VLP and rVSV-EboGPΔM-HAcsM2e could induce broad immune responses against H1N1, H3N2 and H5N1 more than the native HA/NA/M2 (FIG. 9c).

Materials and Methods

Construction of EboGPΔM-HAcsM2, EboGPΔM-tM2e and EboGPΔM-HAH5-1-3 plasmids. To construct EboGPΔM-HAcsM2, EboGPΔM-tM2e and EboGPΔM-HAH5-1-3 plasmids, each DNA encoding HAcsM2, tM2e and HA$_{H5-1-3}$ sequences were synthesized and cloned into an EboGPΔM expressing plasmid, pCAGG-EboGPΔM (49). The M2e polypeptide comprised of two copies of the conserved extracellular domain (24 aa) from human influenza M2, one copy of the extracellular domain (24 aa) from avian influenza and one copy from or swine influenza M2 protein (FIG. 1C) (21). The conserved stalk regions (HAcs) of hemagglutinin (HA) was derived from influenza H5N1, and the polypeptides (HA$_{H5-1-3}$) were selected from the HA head regions from H5N1, H1N1 and H3N2 strains.

To produce different pseudotyped VLPs, each of EboGPΔM-HAcsM2, EboGPΔM-tM2e and EboGPΔM-HA$_{H5-1-3}$ plasmids was co-transfected with a HIV Gag-Pol, packaging vector (pCMV delta 8.2) and a Gluc-encoded ΔRI/ΔE lentiviral vector, which was used to monitor the viral entry ability of the VLPs, as previously described (4, 20).

Cells, antibodies, and chemicals: Human embryonic kidney 293T, THP-1 cells or Mardin-Darby Canine Kidney (MDCK) cell lines were cultured in DMEM or RPMI-1640 medium supplemented with 10% fetal bovine serum (FBS) or 2% FBS for MDCK cells. To obtain macrophages and DCs, THP-1 cells were differentiated into macrophages by treating with 100 ng/ml of Phorbol myristate acetate (PMA) (R&D Systems) or with 100 ng/ml of Granulocyte-macrophages colony-stimulating factor (GM-CSF) (R&D Systems) and Interleukin-4 (IL-4) (R&D Systems) for DCs' differentiation. Also, to obtain MDMs or MDDCs, monocytes were isolated from human peripheral blood mononuclear cells (hPBMCs) and were treated with 10 ng/ml of PMA or 10 ng/ml of GM-CSF and IL-4 respectively for seven (7) days. The M2 monoclonal antibody (14C2: sc-32238) was obtained from Santa Cruz Biotechnology, HA antibody pools (TA500060; TA500059) were obtained from Origene while M2 peptide (RP20206) was obtained from Genescript, and HA peptides were synthesized by Shangai Royobiotech (19CL00157) and recombinant HA (rHA) (40160-V08B1) was obtained from Sino Biologicals. Ebola GP monoclonal antibody (mAb) 42/3.7 was kindly given by Dr. A Takada, Hokkaido University, Japan (34)

Production and characterization of EboGPΔM-HAcsM2, EboGPΔM-tM2e and EboGPΔM-$HA_{H5-1-3}$ pseudotyped VLPs: To produce different pseudotyped VLPs VLPs, 293T cells were co-transfected with pCMV delta 8.2, an ΔRI/ΔE/Gluc lentiviral vector, and each of pCAGG-EboGPΔM-tM2e, pCAGG-EboGPΔM-HAcsM2 or pCAGG-EboGPΔM-$HA_{H5-1-3}$ plasmids as indicated in FIG. 1A. Also, a native HA/NA/M2 VLPs was produced and used as control. After 48 h of post-transfection, cell debris was removed from the supernatant by centrifuging at 3000 rpm for 15 min, after which the VLPs particles were pelleted by ultracentrifugation at 35000 rpm for 1 hour 30 minutes and re-suspended in Endotoxin-free PBS (EMD Millipore Corp). To quantify the virus stocks, HIVGagp24 were measured using p24 ELISA assay and kept in-80° C. for both in vitro infection for viral entry investigation and in vivo immunization experiments. To detect the expression of different viral proteins in VLP particles and cells used to produce the VLPs. The cells and VLPs were lysed by Laemmli buffer and were analyzed using SDS-PAGE and western blot with anti-EboGP MAb 42/3.7, anti-M2 (14C2), anti-HA or anti HIVp24 antibodies.

To test for the cell entry ability of different pseudotyped VLPs, an equal amounts of EbovGPΔM, EboGPΔM-HAcsM2, EboGPΔM-tM2e and EboGPΔM-HAH5-1-3, as adjusted by HIV Gagp24, were used to infect 293T cells, TZMB-1 cells, THP-1 cells, THP-1 differentiated DCs and macrophages, MDMs and MDDCs.

Mice immunization experiments: Female BALB/c mice aged 4-6 weeks used in this study were obtained from the Central Animal Care Facility, the University of Manitoba (with the animal study protocol approval No. 16-012/1 (AC11159)). The mice were divided into four mice per group while each group of mice were immunized as indicated in FIG. 2A. Briefly, each group was immunized subcutaneously by injection with 100 ng (adjusted by HIV p24) of VLPs in 100 μl endotoxin-free PBS on day 0, 28, 56 and blood samples were collected on days 7, 35 and 63. Blood collected was left at room temperature for 1-2 hrs and then was centrifuged at 8,600×g for 3 min. The resulting sera were stored at −20° C. until further analysis.

Influenza anti-M2 and anti-HA antibody measurements by Enzyme-linked Immunosorbent Assay (ELISA): To determine influenza HA and M2 specific antibodies in sera, ELISA plates (NUNC Maxisorp, Thermo Scientific) were coated with 100 μl of M2 or $HA_2$ peptides proteins (1 μg or 2 μg/ml respectively) in a coupling buffer (0.05M carbonate-bicarbonate of pH 9.6) overnight at 4° C. The plates were washed twice after the incubation with 1×PBST and blocked with blocking buffer (1% BSA in PBS) at 37° C. for 1 hr. The serum samples were diluted to 1:100 in primary antibody diluent, then 100 μl of the diluted mouse serum samples were added into each well of the plates and incubated for 2 hrs at 37° C., followed the wash three times, and 100 μl peroxidase-conjugated goat anti-mouse immunoglobulin G (IgG) (GE Healthcare) was added and incubated for one hr at 37° C. The plates were washed five times, and 3',3',5',5' Tetramethylbenzidine (TMB) (Mandel Scientific) was added and incubated for 15 min at room temperature in darkroom. To stop the reaction, 100 μl of 1N HCl was added to each well and the absorbance was measured at 450 nm optical density.

Infection and plaque assay: A subconfluent monolayers cells of MDCK were washed with 1× phosphate-buffered saline (PBS; 137 mM NaCl, 0.3 mM KCl, 0.8 mM Na2HPO4, 0.1 mM KH2PO4) and infected with H1N1 PR8, H3N2 or H5N1 influenza virus strain diluted from $10^{-1}$ to $10^{-10}$ with gel saline for the purpose of plaque assay in a six-well plate as previously described (46). A 0.8% Avicel cells in FBS-free 1×DMEM media (2 mM L-glutamine, 2 mM sodium pyruvate, and 1×MEM nonessential amino acids, and supplemented with 2.5 μg/mL trypsin, 1× gentamicin and 1× amphotericin B) was used to overlay the cells after 1 hour of adsorption in 37° C. The overlaid cells were incubated for 72 hrs at 35° C. for the plaque to form after which the cells were treated with 2% formaldehyde for fixation for 30 minutes before staining with crystal violet for 1 hour. The stained cells were then washed and allowed to stay for 4 hours for calculating the viral titer in the plaque forming unit per ml (PFU/ml).

Plaque reduction neutralization Assay: To achieve plaque reduction neutralization assay, the immunized mice sera were first heat-inactivated at 56° C. for 30 minutes and were serially diluted in two-folds (47). Serum/virus incubation was done using 25 PFU/ml or 50 PFU/ml of respective strains of influenza virus used (H1N1, H3N2, H5N1) for 1 hour at 37° C. and 5% C02. Following the washing of a subconfluent cells of MDCK as previously mentioned, 100 μl of serum/viral mixtures were used to infect the cells, incubated for 1 hour at 37° C. and 5% C02, covered with 0.8% Avicel and incubated at 35° C. and 5% $CO_2$ for 72 hours, fixed with 2% formaldehyde for 30 minutes, stained with crystal violet, washed and observed after hours.

Cytokine detection: Splenocytes from immunized mice have collected aseptically and placed into the cell strainer and was mashed through the cell strainer inside a sterile 50 ml tube using the plunger end of the syringe to make single-cell suspensions. Red blood cells were removed using Ammonium-Chloride-Potassium (ACK) buffer, and the suspended cell was cultured in 48-well plates at a density of 2×106/125 μl with DMEM containing M2 peptide (1 μg/peptide/ml) respectively. After three days of culturing, supernatants were collected and stored at −70° C. for a cytokine detection assay. Cytokine levels were measured in supernatants by using the 8-plex mouse cytokine kit (Bio-Plex Pro; 12002798) purchased from BIORAD. Briefly, 50 μl of 1× anti-cytokine antibody-coupled beads were added to the 96-well flat bottom plate, and the plate was inserted in the magnetic separator for 60 seconds followed by two times wash with wash buffer. Then 50 μl of supernatants and 50 μl incubation buffer were added and incubated for 2 hr at room temperature on an orbital plate shaker. After incubation, the complexes were washed two times using the magnetic separator wash procedure followed by incubation with a 1× biotinylated detector antibody for 1 hour. After washing, the 1× streptavidin-RPE solution was added into the assay well and incubated for 30 min. Finally, the plate wells were washed three times, and the complexes were re-suspended in 150 µl of wash solution, and at least 50 beads were counted during the acquisition in the MAGPIX instrument (EPX370-40045-901, Luminex) according to manufacturer's instructions and xPONENT running protocol setup.

Statistics: Statistical analysis of levels of antibody/cytokine, including the results of G luciferase assay, influenza M2, HA and ELISA, and various cytokine/chemokines were performed using the unpaired t-test (considered significant at $P \geq 0.05$) by GraphPad Prism 5.01 software.

While the preferred embodiments of the invention have been described above, it will be recognized and understood that various modifications may be made therein, and the appended claims are intended to cover all such modifications which may fall within the spirit and scope of the invention.

REFERENCES

1. Agnandji, S. T., A. Huttner, M. E. Zinser, P. Njuguna, C. Dahlke, J. F. Fernandes, S. Yerly, J. A. Dayer, V. Kraehling, R. Kasonta, A. A. Adegnika, M. Altfeld, F. Auderset, E. B. Bache, N. Biedenkopf, S. Borregaard, J. S. Brosnahan, R. Burrow, C. Combescure, J. Desmeules, M. Eickmann, S. K. Fehling, A. Finckh, A. R. Goncalves, M. P. Grobusch, J. Hooper, A. Jambrecina, A. L. Kabwende, G. Kaya, D. Kimani, B. Lell, B. Lemaitre, A. W. Lohse, M. Massinga-Loembe, A. Matthey, B. Mordmuller, A. Nolting, C. Ogwang, M. Ramharter, J. Schmidt-Chanasit, J. Schmiedel, P. Silvera, F. R. Stahl, H. M. Staines, T. Strecker, H. C. Stubbe, B. Tsofa, S. Zaki, P. Fast, V. Moorthy, L. Kaiser, S. Krishna, S. Becker, M. P. Kieny, P. Bejon, P. G. Kremsner, M. M. Addo, and C. A. Siegrist. 2016. Phase 1 Trials of rVSV Ebola Vaccine in Africa and Europe. The New England journal of medicine 374:1647-1660.
2. Ao, Z., J. Huang, X. Tan, X. Wang, T. Tian, X. Zhang, Q. Ouyang, and X. Yao. 2016. Characterization of the single cycle replication of HIV-1 expressing *Gaussia* luciferase in human PBMCs, macrophages, and in CD4(+) T cell-grafted nude mouse. Journal of virological methods 228: 95-102.
3. Ao, Z., A. Patel, K. Tran, X. He, K. Fowke, K. Coombs, D. Kobasa, G. Kobinger, and X. Yao. 2008. Characterization of a trypsin-dependent avian influenza H5N1-pseudotyped HIV vector system for high throughput screening of inhibitory molecules. Antiviral research 79:12-18.
4. Ao, Z., L. Wang, E. J. Mendoza, K. Cheng, W. Zhu, E. A. Cohen, K. Fowke, X. Qiu, G. Kobinger, and X. Yao. 2019. Incorporation of Ebola glycoprotein into HIV particles facilitates dendritic cell and macrophage targeting and enhances HIV-specific immune responses. PLOS ONE 14:e0216949.
5. Banchereau, J., and A. K. Palucka. 2005. Dendritic cells as therapeutic vaccines against cancer. Nature Reviews Immunology 5:296-306.
6. Blanton, L., V. G. Dugan, A. I. A. Elal, N. Alabi, J. Barnes, L. Brammer, A. P. Budd, E. Burns, C. N. Cummings, and S. Garg. 2019. Update: Influenza Activity—United States, Sep. 30, 2018— Feb. 2, 2019. Morbidity and Mortality Weekly Report 68:125.
7. Blut, A. 2009. Influenza virus. Transfusion Medicine and Hemotherapy 36:32.
8. Brandão, J. G., R. J. Scheper, S. a. M. Lougheed, D. T. Curiel, B. W. Tillman, W. R. Gerritsen, A. J. M. Van Den Eertwegh, H. M. Pinedo, H. J. Haisma, and T. D. De Gruijl. 2003. CD40-targeted adenoviral gene transfer to dendritic cells through the use of a novel bispecific single-chain Fv antibody enhances cytotoxic T cell activation. Vaccine 21:2268-2272.
9. Carter, D. M., C. A. Darby, B. C. Lefoley, C. J. Crevar, T. Alefantis, R. Oomen, S. F. Anderson, T. Strugnell, G. Cort-Garcia, and T. U. Vogel. 2016. Design and characterization of a computationally optimized broadly reactive hemagglutinin vaccine for H1N1 influenza viruses. Journal of virology 90:4720-4734.
10. Cummings, J. F., M. L. Guerrero, J. E. Moon, P. Waterman, R. K. Nielsen, S. Jefferson, F. L. Gross, K. Hancock, J. M. Katz, and V. Yusibov. 2014. Safety and immunogenicity of a plant-produced recombinant monomer hemagglutinin-based influenza vaccine derived from influenza A (H1N1) pdm09 virus: a Phase 1 dose-escalation study in healthy adults. Vaccine 32:2251-2259.
11. Evers, T. H., E. M. van Dongen, A. C. Faesen, E. W. Meijer, and M. Merkx. 2006. Quantitative understanding of the energy transfer between fluorescent proteins connected via flexible peptide linkers. Biochemistry 45:13183-13192.
12. Francis, M. E., M. L. King, and A. A. Kelvin. 2019. Back to the Future for Influenza Preimmunity—Looking Back at Influenza Virus History to Infer the Outcome of Future Infections. Viruses 11:122.
13. Fusco, M. L., T. Hashiguchi, R. Cassan, J. E. Biggins, C. D. Murin, K. L. Warfield, S. Li, F. W. Holtsberg, S. Shulenin, H. Vu, G. G. Olinger, D. H. Kim, K. J. Whaley, L. Zeitlin, A. B. Ward, C. Nykiforuk, M. J. Aman, J. D. Berry, and E. O. Saphire. 2015. Protective mAbs and Cross-Reactive mAbs Raised by Immunization with Engineered Marburg Virus GPs. PLoS pathogens 11:e1005016.
14. Giles, B. M., and T. M. Ross. 2011. A computationally optimized broadly reactive antigen (COBRA) based H5N1 VLP vaccine elicits broadly reactive antibodies in mice and ferrets. Vaccine 29:3043-3054.
15. Gostic, K. M., M. Ambrose, M. Worobey, and J. O. Lloyd-Smith. 2016. Potent protection against H5N1 and H7N9 influenza via childhood hemagglutinin imprinting. Science 354:722-726.
16. Grohskopf, L. A., and F. M. Munoz. 2018. 2018-2019 Recommendations for influenza prevention and treatment in children: an update for pediatric providers.
17. Huttner, A., J. A. Dayer, S. Yerly, C. Combescure, F. Auderset, J. Desmeules, M. Eickmann, A. Finckh, A. R. Goncalves, J. W. Hooper, G. Kaya, V. Krahling, S. Kwilas, B. Lemaitre, A. Matthey, P. Silvera, S. Becker, P. E. Fast, V. Moorthy, M. P. Kieny, L. Kaiser, C. A. Siegrist, and V. S.-E. Consortium. 2015. The effect of dose on the safety and immunogenicity of the VSV Ebola candidate vaccine: a randomised double-blind, placebo-controlled phase 1/2 trial. The Lancet. Infectious diseases 15:1156-1166.
18. Kedzierska, K., C. Van de Sandt, and K. R. Short. 2018. Back to the future: lessons learned from the 1918 influenza pandemic. Frontiers in Cellular and Infection Microbiology 8:343.
19. Krammer, F., P. Palese, and J. Steel. 2014. Advances in universal influenza virus vaccine design and antibody mediated therapies based on conserved regions of the hemagglutinin, p. 301-321, Influenza Pathogenesis and Control-Volume II. Springer.
20. Li, S., C. Liu, A. Klimov, K. Subbarao, M. L. Perdue, D. Mo, Y. Ji, L. Woods, S. Hietala, and M. Bryant. 1999. Recombinant influenza A virus vaccines for the pathogenic human A/Hong Kong/97 (H5N1) viruses. The Journal of infectious diseases 179:1132-1138.
21. Liu, W., P. Zou, J. Ding, Y. Lu, and Y. H. Chen. 2005. Sequence comparison between the extracellular domain of M2 protein human and avian influenza A virus provides new information for bivalent influenza vaccine design. Microbes and infection 7:171-177.
22. Martinez, O., L. Tantral, N. Mulherkar, K. Chandran, and C. F. Basler. 2011. Impact of Ebola mucin-like domain on antiglycoprotein antibody responses induced by Ebola virus-like particles. The Journal of infectious diseases 204:S825-S832.
23. Marzi, A., P. Muller, S. L. Hanna, T. Harrer, J. Eisemann, A. Steinkasserer, S. Becker, F. Baribaud, and S. Pohlmann. 2007. Analysis of the Interaction of Ebola Virus Glycoprotein with DC-SIGN (Dendritic Cell-Specific Intercellular Adhesion Molecule 3-Grabbing Nonintegrin) and Its Homologue DC-SIGNR. The Journal of infectious diseases 196:S237-S246.
24. Medina, M. F., G. P. Kobinger, J. Rux, M. Gasmi, D. J. Looney, P. Bates, and J. M. Wilson. 2003. Lentiviral vectors pseudotyped with minimal filovirus envelopes increased gene transfer in murine lung. Molecular Therapy 8:777-789.
25. Meixlsperger, S., C. S. Leung, P. C. RAnmer, M. Pack, L. D. Vanoaica, G. I. Breton, S. Pascolo, A. M. Salazar, A. Dzionek, and J. r. Schmitz. 2012. CD141+ dendritic cells produce prominent amounts of IFN-I± after dsRNA recognition and can be targeted via DEC-205 in humanized mice. Blood:blood-2012-2012-473413.
26. Mullarkey, C. E., M. J. Bailey, D. A. Golubeva, G. S. Tan, R. Nachbagauer, W. He, K. E. Novakowski, D. M. Bowdish, M. S. Miller, and P. Palese. 2016. Broadly neutralizing hemagglutinin stalk-specific antibodies induce potent phagocytosis of immune complexes by neutrophils in an Fc-dependent manner. MBio 7:e01624-01616.
27. Musthaq, S. K. S., S. R. Kumar, M. Szyporta, and J. Kwang. 2014. Immunization with baculovirus displayed H6 hemagglutinin vaccine protects mice against lethal H6 influenza virus challenge. Antiviral research 109:42-53.
28. Nickol, M. E., and J. Kindrachuk. 2019. A year of terror and a century of reflection: perspectives on the great influenza pandemic of 1918&€"1919. BMC infectious diseases 19:117.
29. Nohynek, H., J. Jokinen, M. Partinen, O. Vaarala, T. Kirjavainen, J. Sundman, S.-L. Himanen, C. Hublin, I. Julkunen, and P. i. OlsA©n. 2012. AS03 adjuvanted AH1N1 vaccine associated with an abrupt increase in the incidence of childhood narcolepsy in Finland. PloS one 7:e33536.
30. Olejnik, J., A. Forero, L. R. D, A. J. Hume, W. A. Manhart, A. Nishida, A. Marzi, M. G. Katze, H. Ebihara, and A. L. Rasmussen. 2017. Ebolaviruses associated with differential pathogenicity induce distinct host responses in human macrophages. Journal of virology:JVI. 00179-00117.
31. Querec, T., S. Bennouna, S. Alkan, Y. Laouar, K. Gorden, R. Flavell, S. Akira, R. Ahmed, and B. Pulendran. 2006. Yellow fever vaccine YF-17D activates multiple dendritic cell subsets via TLR2, 7, 8, and 9 to stimulate polyvalent immunity. Journal of Experimental Medicine 203:413-424.
32. Rhein, B. A., and W. J. Maury. 2015. Ebola virus entry into host cells: Identifying therapeutic strategies. Current clinical microbiology reports 2:115-124.
33. Scorza, F. B., V. Tsvetnitsky, and J. J. Donnelly. 2016. Universal influenza vaccines: Shifting to better vaccines. Vaccine 34:2926-2933.
34. Takada, A., H. Ebihara, H. Feldmann, T. W. Geisbert, and Y. Kawaoka. 2007. Epitopes required for antibody-dependent enhancement of Ebola virus infection. The Journal of infectious diseases 196:S347-S356.
35. Tong, S., X. Zhu, Y. Li, M. Shi, J. Zhang, M. Bourgeois, H. Yang, X. Chen, S. Recuenco, and J. Gomez. 2013. New world bats harbor diverse influenza A viruses. PLoS pathogens 9:e1003657.
36. Tsybalova, L. M., L. A. Stepanova, M. A. Shuklina, E. S. Mardanova, R. Y. Kotlyarov, M. V. Potapchuk, S. A. Petrov, E. A. Blokhina, and N. V. Ravin. 2018. Combination of M2e peptide with stalk HA epitopes of influenza A virus enhances protective properties of recombinant vaccine. PloS one 13:e0201429.
37. Turley, C. B., R. E. Rupp, C. Johnson, D. N. Taylor, J. Wolfson, L. Tussey, U. Kavita, L. Stanberry, and A. Shaw. 2011. Safety and immunogenicity of a recombinant M2eâ€"flagellin influenza vaccine (STF2. 4×M2e) in healthy adults. Vaccine 29:5145-5152.
38. Uranowska, K., J. Tyborowska, A. Jurek, B. a. Szewczyk, and B. Gromadzka. 2014. Hemagglutinin stalk domain from H5N1 strain as a potentially universal antigen. Acta Biochimica *Polonica* 61.
39. Valkenburg, S. A., V. V. A. Mallajosyula, O. T. W. Li, A. W. H. Chin, G. Carnell, N. Temperton, R. Varadarajan, and L. L. M. Poon. 2016. Stalking influenza by vaccination with pre-fusion headless HA mini-stem. Scientific reports 6:22666.
40. van Doorn, E., O. Pleguezuelos, H. Liu, A. Fernandez, R. Bannister, G. Stoloff, F. Oftung, S. Norley, A. Huckriede, and H. W. Frijlink. 2017. Evaluation of the immunogenicity and safety of different doses and formulations of a broad spectrum influenza vaccine (FLU-v) developed by SEEK: study protocol for a single-center, randomized, double-blind and placebo-controlled clinical phase IIb trial. BMC infectious diseases 17:241.
41. van Rosmalen, M., M. Krom, and M. Merkx. 2017. Tuning the Flexibility of Glycine-Serine Linkers To Allow Rational Design of Multidomain Proteins. Biochemistry 56:6565-6574.
42. Waldo, G. S., B. M. Standish, J. Berendzen, and T. C. Terwilliger. 1999. Rapid protein-folding assay using green fluorescent protein. Nature biotechnology 17:691-695.
43. Wang, L., A. Hess, T. Z. Chang, Y.-C. Wang, J. A. Champion, R. W. Compans, and B.-Z. Wang. 2014. Nanoclusters self-assembled from conformation-stabilized influenza M2e as broadly cross-protective influenza vaccines. Nanomedicine: Nanotechnology, Biology and Medicine 10:473-482.
44. Weir, J. P., and M. F. Gruber. 2019. An overview of the regulation of influenza vaccines in the United States. Influenza and other respiratory viruses 10:354-360.
45. Wu, P., J. Lu, X. Zhang, M. Mei, L. Feng, D. Peng, J. Hou, S.-M. Kang, X. Liu, and Y. Tang. 2017. Single dose of consensus hemagglutinin-based virus-like particles vaccine protects chickens against divergent H5 subtype influenza viruses. Frontiers in immunology 8:1649.

46. Zahedi-Amiri, A., G. L. Sequiera, S. Dhingra, and K. M. Coombs. 2019. Influenza a virus-triggered autophagy decreases the pluripotency of human-induced pluripotent stem cells. Cell death & disease 10:337.

47. Zaneti, A. B., M. M. Yamamoto, F. B. Sulczewski, B. d. S. Almeida, H. F. S. Souza, N. I. S. Ferreira, D. L. N. F. Maeda, N. S. Sales, D. S. Rosa, and L. Ferreira. 2019. Dendritic cell targeting using a DNA vaccine induces specific antibodies and CD4+ T cells to the dengue virus envelope protein domain III. Frontiers in immunology 10:59.

48. Zaneti, A. B., M. M. Yamamoto, F. B. Sulczewski, B. d. S. Almeida, H. F. S. Souza, N. I. S. Ferreira, D. L. N. F. Maeda, N. S. Sales, D. S. Rosa, L. C. d. S. Ferreira, and S. B. Boscardin. 2019. Dendritic Cell Targeting Using a DNA Vaccine Induces Specific Antibodies and CD4+ T Cells to the Dengue Virus Envelope Protein Domain III. Frontiers in Immunology 10.

49. Zhang, X., Z. Ao, A. Bello, X. Ran, S. Liu, J. Wigle, G. Kobinger, and X. Yao. 2016. Characterization of the inhibitory effect of an extract of Prunella vulgaris on Ebola virus glycoprotein (GP)-mediated virus entry and infection. Antiviral research 127:20-31.

The invention claimed is:

1. A fusion protein comprising an influenza virus surface protein peptide inserted in the mucin-like domain of a Filoviridae Virus glycoprotein wherein the influenza virus surface protein is selected from the group consisting of hemagglutinin and matrix-2 and the influenza virus surface protein peptide comprises 6 or more consecutive amino acids of the influenza virus surface protein.

2. The fusion protein according to claim 1 wherein the peptide comprises 6 or more consecutive amino acids of a conserved region of hemagglutinin or matrix-2 or 6 or more consecutive amino acids of globular head domain of hemagglutinin.

3. The fusion protein according to claim 1 wherein the fusion peptide comprises more than one influenza virus surface protein peptide and each respective influenza virus surface protein peptide is separated from an adjacent influenza virus surface protein peptide by a spacer.

4. The fusion protein according to claim 1 wherein the mucin-like domain is a tolerated deletion of the mucin-like domain.

5. The fusion peptide according to claim 1 wherein the fusion peptide comprises the amino acid sequence as set forth in SEQ ID NO:1, SEQ ID NO:2 or SEQ ID NO:3.

6. A method of targeting an influenza virus surface protein peptide to a dendritic cell comprising:
providing virus-like particles comprising as glycoprotein a Filoviridae Virus glycoprotein fusion protein comprising an influenza virus surface protein peptide inserted in the mucin-like domain of the Filoviridae Virus glycoprotein wherein the influenza virus surface protein is selected from the group consisting of hemagglutinin and matrix-2 and the influenza virus surface protein peptide comprises 6 or more consecutive amino acids of the influenza virus surface protein; and
immunizing an individual with the virus-like particles.

7. The method according to claim 6 wherein the Filoviridae virus is Ebola virus or Marburg virus.

8. The method according to claim 6 wherein the influenza virus surface protein peptide comprises 6 or more consecutive amino acids of a conserved region of hemagglutinin or matrix-2 or 6 or more consecutive amino acids of globular head domain of hemagglutinin.

9. The method according to claim 6 wherein the fusion peptide comprises more than one influenza virus surface protein peptide and each respective influenza virus surface protein peptide is separated from an adjacent influenza virus surface protein peptide by a spacer.

10. The method according to claim 6 wherein the mucin-like domain is a tolerated deletion of the mucin-like domain.

11. The method according to claim 6 wherein the fusion peptide comprises the amino acid sequence as set forth in SEQ ID NO:1, SEQ ID NO: 2 or SEQ ID NO: 3.

12. A method of eliciting an immune response against an influenza surface protein peptide in an individual comprising:
providing virus-like particles comprising as glycoprotein a Filoviridae Virus glycoprotein fusion protein comprising an influenza virus surface protein peptide inserted in the mucin-like domain of the Filoviridae Virus glycoprotein wherein the influenza virus surface protein is selected from the group consisting of hemagglutinin and matrix-2 and the influenza virus surface protein peptide comprises 6 or more consecutive amino acids of the influenza virus surface protein; and
immunizing an individual in need of immunization against influenza virus with an effective amount of the virus-like particles.

13. The method according to claim 12 wherein the Filoviridae virus is Ebola virus or Marburg virus.

14. The method according to claim 12 wherein the peptide comprises 6 or more consecutive amino acids of a conserved region of hemagglutinin or matrix-2 or 6 or more consecutive amino acids of globular head domain of hemagglutinin.

15. The method according to claim 12 wherein the fusion peptide comprises more than one influenza virus surface protein peptide and each respective influenza virus surface protein peptide is separated from an adjacent influenza virus surface protein peptide by a spacer.

16. The method according to claim 12 wherein the mucin-like domain is a tolerated deletion of the mucin-like domain.

17. The method according to claim 12 wherein the fusion peptide comprises the amino acid sequence as set forth in SEQ ID No:1, SEQ ID No: 2 or SEQ ID No. 3.

\* \* \* \* \*

SEQUENCE LISTING

```
<160> NUMBER OF SEQ ID NOS: 3

<210> SEQ ID NO 1
<211> LENGTH: 281
<212> TYPE: PRT
<213> ORGANISM: artificial
<220> FEATURE:
<223> OTHER INFORMATION: artificial fusion peptide comprising head COBRA
      H5/H1/H3 regions
<220> FEATURE:
<221> NAME/KEY: MISC_FEATURE
<222> LOCATION: (1)..(5)
<223> OTHER INFORMATION: spacer
<220> FEATURE:
<221> NAME/KEY: MISC_FEATURE
<222> LOCATION: (6)..(66)
<223> OTHER INFORMATION: H5 head COBRA sequence
<220> FEATURE:
<221> NAME/KEY: MISC_FEATURE
<222> LOCATION: (67)..(71)
<223> OTHER INFORMATION: spacer
<220> FEATURE:
<221> NAME/KEY: MISC_FEATURE
<222> LOCATION: (72)..(111)
<223> OTHER INFORMATION: head COBRA H1 sequence
<220> FEATURE:
<221> NAME/KEY: MISC_FEATURE
<222> LOCATION: (112)..(116)
<223> OTHER INFORMATION: spacer
<220> FEATURE:
<221> NAME/KEY: MISC_FEATURE
<222> LOCATION: (117)..(132)
<223> OTHER INFORMATION: head COBRA H1 sequence
<220> FEATURE:
<221> NAME/KEY: MISC_FEATURE
<222> LOCATION: (119)..(183)
<223> OTHER INFORMATION: spacer
<220> FEATURE:
<221> NAME/KEY: MISC_FEATURE
<222> LOCATION: (133)..(137)
<223> OTHER INFORMATION: spacer
<220> FEATURE:
<221> NAME/KEY: MISC_FEATURE
<222> LOCATION: (138)..(178)
<223> OTHER INFORMATION: head COBRA H1 sequence
<220> FEATURE:
<221> NAME/KEY: MISC_FEATURE
<222> LOCATION: (184)..(276)
<223> OTHER INFORMATION: head COBRA H3 sequence
<220> FEATURE:
<221> NAME/KEY: MISC_FEATURE
<222> LOCATION: (277)..(281)
<223> OTHER INFORMATION: spacer

<400> SEQUENCE: 1

Gly Pro Gly Pro Gly Glu Lys Thr His Asn Gly Lys Leu Cys Asp Leu
1               5                   10                  15

Asp Gly Val Lys Pro Leu Ile Leu Arg Asp Cys Ser Val Ala Gly Trp
            20                  25                  30
```

Leu Leu Gly Asn Pro Met Cys Asp Glu Phe Ile Asn Val Pro Glu Trp
            35                  40                  45

Ser Tyr Ile Val Glu Lys Ala Asn Pro Ala Asn Asp Leu Cys Tyr Pro
 50                  55                  60

Gly Asn Gly Pro Gly Pro Gly Cys Tyr Pro Gly Tyr Phe Ala Asp Tyr
 65                  70                  75                  80

Glu Glu Leu Arg Glu Gln Leu Ser Ser Val Ser Ser Phe Glu Arg Phe
                 85                  90                  95

Glu Ile Phe Pro Lys Glu Ser Ser Trp Pro Asn His Thr Val Thr Gly
                100                 105                 110

Pro Gly Pro Gly Glu Lys Glu Val Leu Val Leu Trp Gly Val His His
            115                 120                 125

Pro Ser Asn Ile Gly Pro Gly Pro Gly Pro Lys Val Arg Asp Gln Glu
130                 135                 140

Gly Arg Ile Asn Tyr Tyr Trp Thr Leu Leu Glu Pro Gly Asp Thr Ile
145                 150                 155                 160

Ile Phe Glu Ala Asn Gly Asn Leu Ile Ala Pro Trp Tyr Ala Phe Ala
                165                 170                 175

Leu Ser Gly Pro Gly Pro Gly Asn Asn Glu Lys Phe Asp Lys Leu Tyr
            180                 185                 190

Ile Trp Gly Val His His Pro Gly Thr Asp Ser Asp Gln Ile Ser Leu
            195                 200                 205

Tyr Ala Gln Ala Ser Gly Arg Ile Thr Val Ser Thr Lys Arg Ser Gln
            210                 215                 220

Gln Thr Val Ile Pro Asn Ile Gly Ser Arg Pro Arg Val Arg Asp Val
225                 230                 235                 240

Ser Ser Arg Ile Ser Ile Tyr Trp Thr Ile Val Lys Pro Gly Asp Ile
                245                 250                 255

Leu Leu Ile Asn Ser Thr Gly Asn Leu Ile Ala Pro Arg Gly Tyr Phe
            260                 265                 270

Lys Ile Arg Ser Gly Pro Gly Pro Gly
            275                 280

<210> SEQ ID NO 2
<211> LENGTH: 194
<212> TYPE: PRT
<213> ORGANISM: artificial
<220> FEATURE:
<223> OTHER INFORMATION: artificial fusion peptide of HA stalk region
      and M2eh region
<220> FEATURE:
<221> NAME/KEY: MISC_FEATURE
<222> LOCATION: (1)..(5)
<223> OTHER INFORMATION: spacer
<220> FEATURE:
<221> NAME/KEY: MISC_FEATURE
<222> LOCATION: (31)..(33)
<223> OTHER INFORMATION: spacer
<220> FEATURE:
<221> NAME/KEY: MISC_FEATURE
<222> LOCATION: (71)..(73)
<223> OTHER INFORMATION: spacer
<220> FEATURE:
<221> NAME/KEY: MISC_FEATURE
<222> LOCATION: (93)..(95)
<223> OTHER INFORMATION: spacer
<220> FEATURE:
<221> NAME/KEY: MISC_FEATURE
<222> LOCATION: (192)..(194)
<223> OTHER INFORMATION: spacer

<400> SEQUENCE: 2

-continued

Gly Pro Gly Pro Ser Ala Glu Gln Val Asp Thr Ile Met Glu Lys Asn
1               5                   10                  15

Val Thr Val Thr His Ala Gln Asp Ile Leu Glu Lys Thr His Gly Ser
            20                  25                  30

Ala Ile Asn Ser Ser Met Pro Phe His Asn Ile His Pro Leu Thr Ile
        35                  40                  45

Gly Glu Cys Pro Lys Tyr Val Lys Ser Asn Arg Leu Val Leu Ala Thr
    50                  55                  60

Gly Leu Arg Asn Ser Pro Gly Ser Ala Ser Leu Leu Thr Glu Val Glu
65              70                  75                  80

Thr Pro Ile Arg Asn Glu Trp Gly Cys Arg Cys Asn Gly Ser Ala Ser
                85                  90                  95

Thr Gln Lys Ala Ile Asp Gly Val Thr Asn Lys Val Asn Ser Ile Ile
            100                 105                 110

Asp Lys Met Asn Thr Gln Phe Glu Ala Val Gly Arg Glu Phe Asn Asn
            115                 120                 125

Leu Glu Arg Arg Ile Glu Asn Leu Asn Lys Lys Met Glu Asp Gly Phe
        130                 135                 140

Leu Asp Val Trp Thr Tyr Asn Ala Glu Leu Leu Val Leu Met Glu Asn
145                 150                 155                 160

Glu Arg Thr Leu Asp Phe His Asp Ser Asn Val Lys Asn Leu Tyr Asp
                165                 170                 175

Lys Val Arg Arg Gln Leu Arg Asp Asn Ala Lys Glu Leu Gly Asn Gly
            180                 185                 190

Ser Ala

<210> SEQ ID NO 3
<211> LENGTH: 111
<212> TYPE: PRT
<213> ORGANISM: artificial
<220> FEATURE:
<223> OTHER INFORMATION: fusion protein comprising M2e regions
<220> FEATURE:
<221> NAME/KEY: MISC_FEATURE
<222> LOCATION: (1)..(4)
<223> OTHER INFORMATION: spacer
<220> FEATURE:
<221> NAME/KEY: MISC_FEATURE
<222> LOCATION: (27)..(30)
<223> OTHER INFORMATION: spacer
<220> FEATURE:
<221> NAME/KEY: MISC_FEATURE
<222> LOCATION: (54)..(57)
<223> OTHER INFORMATION: spacer
<220> FEATURE:
<221> NAME/KEY: MISC_FEATURE
<222> LOCATION: (81)..(84)
<223> OTHER INFORMATION: spacer
<220> FEATURE:
<221> NAME/KEY: MISC_FEATURE
<222> LOCATION: (108)..(111)
<223> OTHER INFORMATION: spacer

<400> SEQUENCE: 3

```
Gly Gly Ser Ser Leu Leu Thr Glu Val Glu Thr Pro Ile Arg Asn Glu
1               5                   10                  15

Trp Gly Cys Arg Cys Asn Asp Ser Ser Asp Gly Gly Gly Ser Ser Leu
            20                  25                  30

Leu Thr Glu Val Glu Thr Pro Thr Arg Asn Gly Trp Glu Cys Lys Cys
        35                  40                  45

Ser Asp Ser Ser Asp Gly Gly Gly Ser Ser Leu Leu Thr Glu Val Glu
    50                  55                  60
```

-continued

```
Thr Pro Ile Arg Asn Glu Trp Gly Cys Arg Cys Asn Asp Ser Ser Asp
 65              70                  75                  80

Gly Gly Gly Ser Ser Leu Leu Thr Glu Val Glu Thr Pro Ile Arg Asn
                 85                  90                  95

Gly Trp Glu Cys Arg Cys Asn Asp Ser Ser Asp Gly Gly Gly Ser
                100                 105                 110
```